United States Patent
Murakami et al.

(10) Patent No.: US 6,381,356 B1
(45) Date of Patent: Apr. 30, 2002

(54) METHOD AND APPARATUS FOR INSPECTING HIGH-PRECISION PATTERNS

(75) Inventors: Shingo Murakami; Tsuyoshi Yamane; Yukio Ogura; Katsuhiko Nakatani; Yoshiaki Aida, all of Tokyo (JP)

(73) Assignee: NEC Corporation, Tokyo (JP)

( * ) Notice: Subject to any disclaimer, the term of this patent is extended or adjusted under 35 U.S.C. 154(b) by 0 days.

(21) Appl. No.: 08/954,263

(22) Filed: Oct. 20, 1997

(30) Foreign Application Priority Data

Oct. 23, 1996 (JP) .............................................. 8-280828

(51) Int. Cl.[7] ................................................ G06K 9/00
(52) U.S. Cl. ........................ 382/141; 382/145; 382/149; 382/254; 382/266; 356/239.2; 356/237.1; 356/237.6; 356/243.8
(58) Field of Search ................................. 382/141, 143, 382/145, 147, 148, 149, 151, 184, 254, 255, 266; 356/239.2, 239.3, 237.3, 237.4, 237.6, 248.8; 430/5, 30

(56) References Cited

U.S. PATENT DOCUMENTS

| | | | | |
|---|---|---|---|---|
| 4,330,205 A | * | 5/1982 | Murakami et al. .......... 356/237 |
| 4,550,374 A | * | 10/1985 | Meshman et al. .......... 364/488 |
| 4,641,257 A | * | 2/1987 | Ayata .......................... 364/559 |
| 4,794,648 A | * | 12/1988 | Ayata et al. .................... 382/8 |
| 4,936,665 A | * | 6/1990 | Whitney ..................... 350/440 |
| 4,955,062 A | * | 9/1990 | Terui ............................. 382/2 |
| 5,179,422 A | | 1/1993 | Peterson ................ 250/559.41 |
| 5,528,360 A | * | 6/1996 | Kohno ........................ 356/390 |
| 5,544,256 A | * | 8/1996 | Brecher et al. ............. 382/149 |
| 5,563,702 A | * | 10/1996 | Emery et al. ................ 356/237 |
| 5,572,598 A | | 11/1996 | Wihl et al. .................. 356/394 |
| 5,909,282 A | * | 6/1999 | Kulawiec ..................... 356/357 |
| 5,986,235 A | * | 11/1999 | Canella .................. 219/121.68 |

FOREIGN PATENT DOCUMENTS

| | | |
|---|---|---|
| DE | 39 18 412 | 2/1990 |
| DE | 196 26 261 | 1/1997 |
| EP | 0 532 927 | 3/1993 |
| EP | 0 567 701 | 11/1993 |

* cited by examiner

*Primary Examiner*—Matthew C. Bella
*Assistant Examiner*—Sheela Chawan
(74) *Attorney, Agent, or Firm*—Young & Thompson

(57) ABSTRACT

A device and method for inspecting a test piece with a laser beam in which the laser beam is divided into plural beams, and each of the plural beams has an identification marker, such as a particular polarity or intensity. Each of the marked beams, scans a different portion of the test piece to reduce the time needed to inspect the test piece.

7 Claims, 18 Drawing Sheets

METHOD AND APPARATUS FOR INSPECTING HIGH-PRECISION PATTERNS

BACKGROUND OF THE INVENTION

1. Field of the Invention

The present invention relates to an inspection method and an inspection apparatus associated with inspecting the external views of the reticles for large scale integrated circuits (LSI) fabrication or the patterns of LSIs themselves.

2. Description of the Related Art

Conventionally, it is a general practice that reticles for LSI fabrication or the patterns of LSIs themselves are inspected by providing two optical systems using metallurgical microscopes, simultaneously observing identical portions of the patterns under test, and obtaining a difference between these portions to detect a defect.

As the LSI patterns have decreased in size, the above-mentioned conventional method can no longer cope with the recent LSI patterns due to the limitation in resolving power. To overcome this problem, a method as disclosed in U.S. Pat. No. 5,572,598 was proposed. In this method, a laser beam having good convergence characteristics is used as the light source. This laser is collected into a microscopic spot. The surface of a test piece, such as a pattern for LSI fabrication, is scanned with this laser beam. An image of the observed surface of the test piece is constructed based on the variation in light quantity of the laser beam transmitted through or reflected from the test piece.

The above-mentioned method, however, uses a technique in which the test piece is scanned with the laser spot in a two-dimensional manner to obtain an observed image. Therefore, as compared with the conventional technique in which an observed image is obtained in a batch by using a camera or an equivalent detector in a single-dimensional or two-dimensional manner, the time for observed image detection increases remarkably.

Moreover, as the resolving power for inspection continues to increase, there is also a drastic increase in data processing requirements. It is therefore strongly desired to shorten the detection time for the observed image of test pieces.

SUMMARY OF THE INVENTION

It is therefore an object of the present invention to solve the above-mentioned problems by providing an inspection method and an inspection apparatus that shortens the time for inspecting the reticles for LSI fabrication semiconductor chips, or the patterns of LSIs themselves (hereinafter referred to as "test pieces") and that have higher precision than the prior art.

In carrying out the invention and according to one aspect thereof, a method of inspecting a high-precision pattern by scanning a surface of a test piece with a laser beam and using at least one of a light beam reflected from the surface of the test piece and a light beam transmitted through the surface of the test piece includes the steps of: branching the laser beam into a plurality of laser beams in order to scan the surface of the test piece with the laser beam as the plurality of branched scan laser beams simultaneously; assigning an identification marker to each of the plurality of branched scan laser beams; and identifying each of the plurality of branched scan laser beams by the identification marker to provide an image of the surface of the test piece corresponding to each of the identified branched scan laser beams.

The laser beam branching step may include a step for splitting the laser beam into two, a step for tilting the optical axis of one of the split laser beams, and a step for synthesizing the two split laser beams. The identification marker may either be a different polarized state assigned to each branched scan laser beam or a variation in light intensity assigned to each branched scan laser beam in a time division manner.

Preferably, the laser beam has an ultraviolet wavelength.

In carrying out the invention and according to another aspect thereof, an apparatus for inspecting a high-precision pattern by scanning a surface of a test piece with a laser beam and using at least one of a light beam reflected from the surface of the test piece and a light beam transmitted through the surface of the test piece may include: a scanning means for scanning the surface of the test piece with the laser beam; a laser beam branching means for branching the laser beam into a plurality of laser beams in order to scan the surface of the test piece with the laser beam as the plurality of branched scan laser beams simultaneously; an identification marker assigning means for assigning an identification marker to each of the plurality of branched scan laser beams; a radiating means for radiating the plurality of branched scan laser beams assigned with the identification markers onto the surface of the test piece; an image signal detecting means for detecting at least one of the light reflected from the surface of the test piece and the light transmitted through the surface of the test piece; a system control having an image processing unit for identifying each of the plurality branched scan laser beams by the identification markers and detecting a defect by obtaining an image of the surface of the test piece by using a detect signal obtained from the image signal detecting means, an image display section for displaying an desired image, and an input section for inputting data from outside; and an XY stage for holding the test piece to drive the same in X-axis and Y-axis directions.

The laser beam branching means may include a splitting means for splitting the laser beam into two, an optical axis changing means for tilting the optical axis of one of the two split laser beams, and a synthesizing means for synthesizing the two split laser beams.

The laser beam branching means may be a plurality of unit laser beam branching means provided in at least one of parallel and series arrangements, the unit laser beam branching means including one splitting means for splitting the laser beam into two, one optical axis changing means for tilting the optical axis of one of the two split laser beams, and one synthesizing means for synthesizing the two split laser beams.

The optical axis changing means may include a wedge-shaped glass plate.

The identification marker to be assigned by the identification marker assigning means may be a different polarized state assigned to each of the plurality of branched scan laser beams or a variation in a light intensity assigned to each of the plurality of branched scan laser beams in a time division manner.

The identification marker assigning means for assigning the variation in light intensity that provides the identification marker may have an ultrasonic modulating means for performing analog modulation on each of the plurality of branched scan laser beams to change a light intensity thereof and a modulation signal generating means for outputting a modulation signal to the ultrasonic modulating means in a predetermined time division manner.

Further, preferably, the laser beam may have an ultraviolet wavelength.

The laser beam radiated from the laser light source is branched into a plurality of laser beams by the laser beam branching means, so that the test piece surface can be scanned with the plurality of laser beams for scanning predetermined ranges of the surface. By combining, in at least one of parallel and series arrangements, a plurality of unit laser beam splitting means for splitting the laser beam into two, tilting the optical axis of one of the split laser beams, and synthesizing the split laser beams, a desired number of branched scan laser beams including an odd number thereof can be generated.

By assigning an identification marker to each of the branched scan laser beams, the branched scan laser beams can be identified in the detect signal obtained from the image signal detecting means for detecting at least one of the light beams reflected from and transmitted through the test piece surface. Consequently, an image of the wide test piece surface can be obtained in a short time for defect detection.

By the XY stage for holding the test piece and driving the same in the X-axis and Y-axis directions relative to the laser beam radiation position, the test piece can be scanned in the X-axis direction. When the test piece has been scanned in the X-axis direction once, the test piece is step-fed in the Y-axis direction to be scanned in the direction opposite to the X-axis direction. This operation is repeated to scan all over the subject area of the test piece in a scan width in which the plurality of branched scan laser beams are arranged side by side.

A first advantage of the present invention is that the inspection method in which the ultrasonic deflector and the technique of splitting the laser beam into two are combined can expand the image signal detection per unit time from conventional 500 points to 1000 points. Further splitting of the laser beam can further increase the number of points per unit time. Consequently, the time for inspecting defects of reticles for LSI fabrication, for example, can be shortened to enhance productivity. This also significantly reduces the cost of LSI itself.

A second advantage of the present invention is that the UV light having wavelength of 363.8 nm is used for the light source, so that, as compared with the prior-art resolution of about 0.3 $\mu$m for defect detection, a defect size as small as 0.1 $\mu$m can be realized, enabling the defect detection of higher precision patterns than the prior art. This provides an extremely effective inspection technique for the recent LSI fabrication reticles for example that are getting more microscopic in feature.

A third advantage of the present invention is that, compared with the prior-art technique in which the same laser light source is used for both illumination and autofocusing, optical axis adjustment and the like can be made easily and, at the same time, the accuracy of autofocus detection can be enhanced because He—Ne laser (wavelength 632.8 nm) is used for the autofocusing light source independently of the light source for illumination.

A fourth advantage of the present invention is that highly precise alignment of test piece can be performed by using the stage having 3 degrees, of freedom, i.e. x, y and $\theta$ directions.

DETAILED DESCRIPTION OF THE PREFERRED EMBODIMENT

Figure 1:
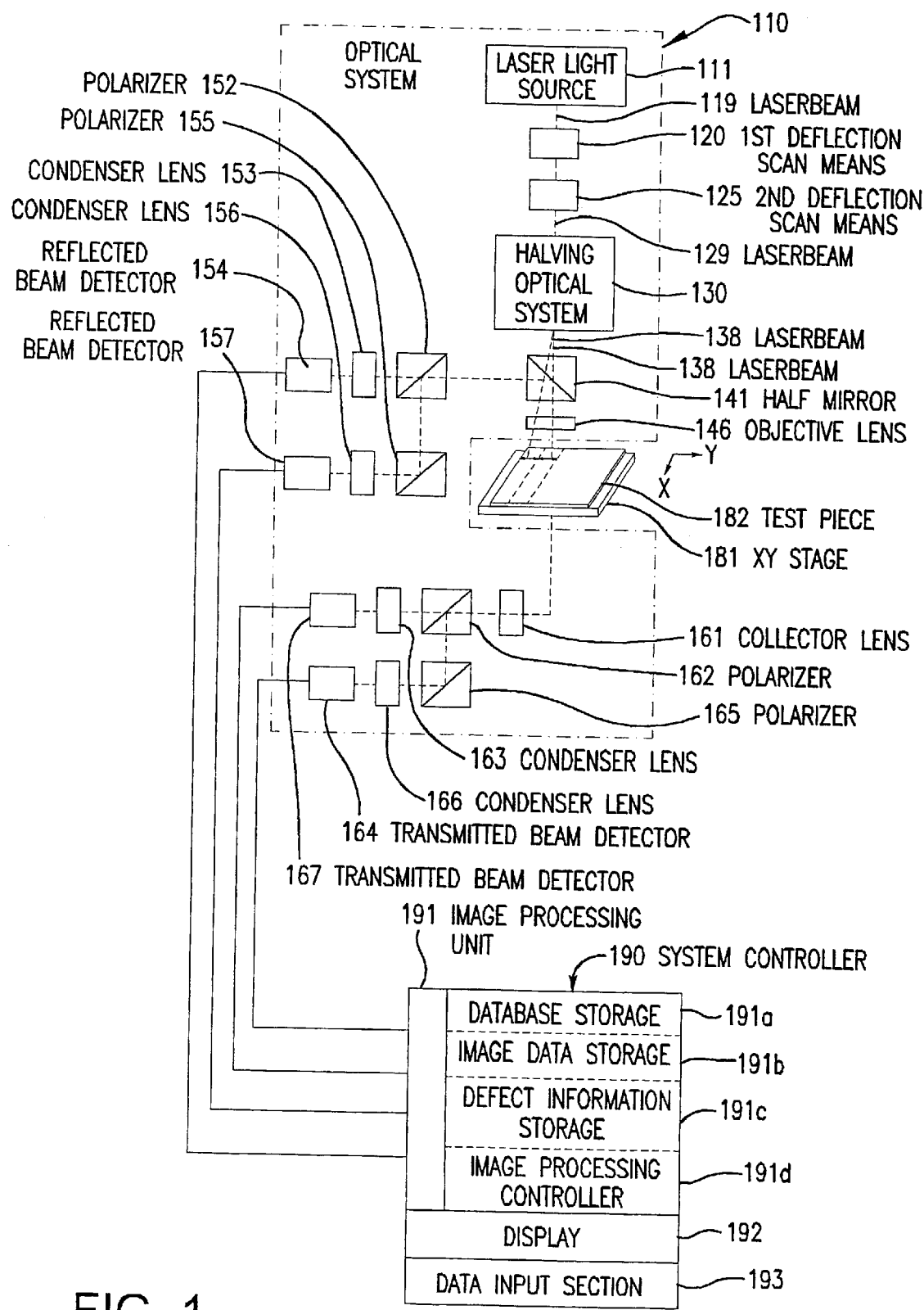
FIG. 1 is a general block diagram illustrating an apparatus for inspecting high-precision patterns.
Figure 2:
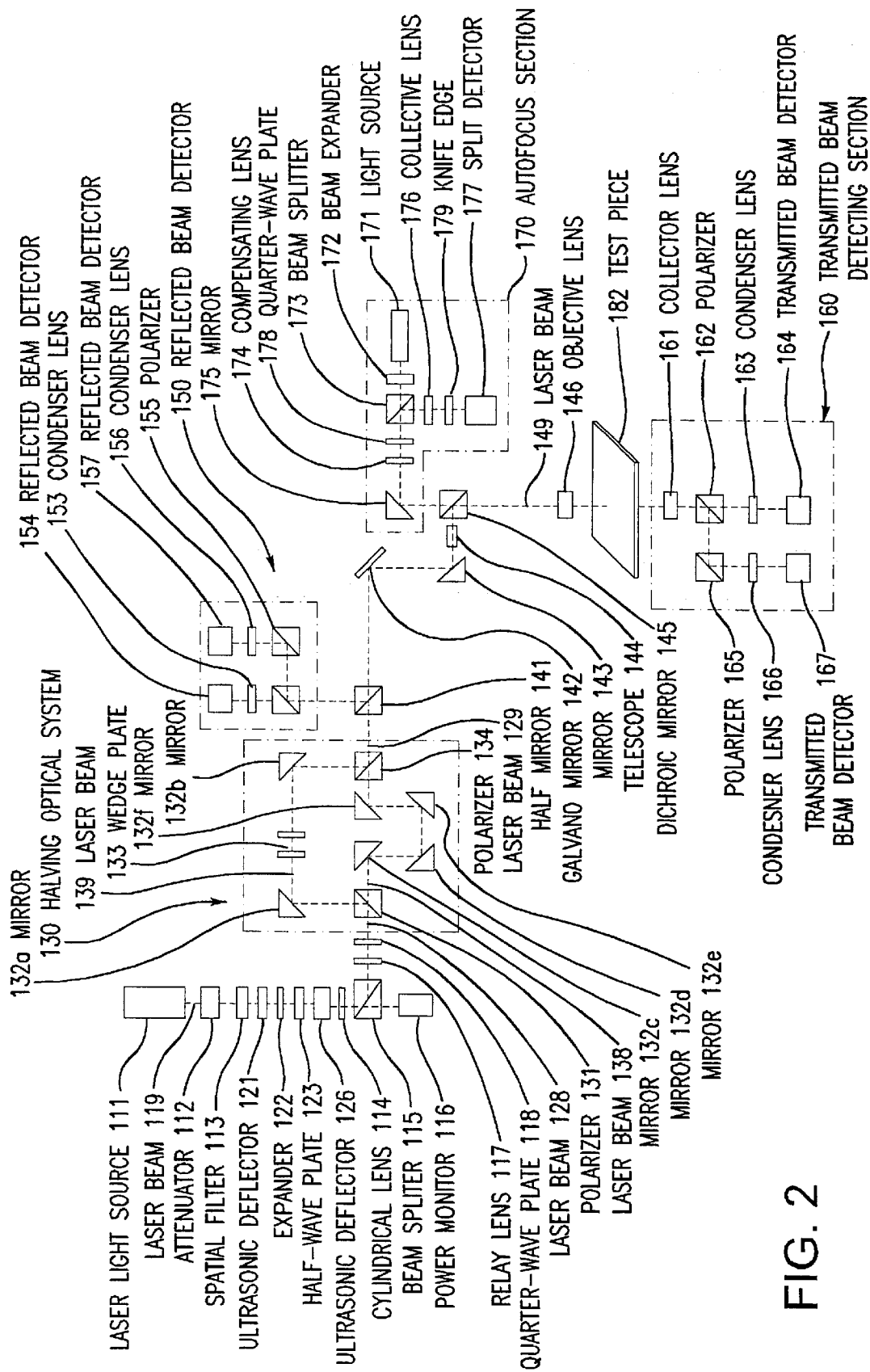
FIG. 2 is a detailed block diagram illustrating an optical system in the inspection apparatus practiced as the first embodiment of the invention.

The following describes in detail a first embodiment of the present invention with reference to FIGS. 1 and 2. The high-precision pattern inspection apparatus according to the present invention is an inspection apparatus for locating defects, for example, errors of shape, size, registration and lack of pattern and so on, of the test pieces.

As shown in FIG. 1, the high-precision pattern inspection apparatus according to the present invention is composed of the optical system 110 including the laser light source 111 providing illumination light, the deflection scan means 120 and 125 for deflectively scanning the laser beam 119 output from the laser light source, the halving optical system 130 that is a laser beam branching means for splitting the laser beam into two, and other optical units, the XY stage 181 for holding thereon the test piece 182 to be inspected, and the system controller 190 having the display 192 and the data input section 193.

The XY stage 181 comprises an X table (not shown) that is automatically fed in the X-axis direction and a Y table that is step-fed in the Y-axis direction. Each table is driven by a mechanism (not shown) that converts the rotary movement of an AC servo motor into the linear movement by a ball screw.

The following describes the optical system 110 with reference to FIG. 2 in detail. This optical system 110 is composed of a first transmission system for deflecting the laser beam and transmitting the resultant laser beam to the halving optical system 130, the halving optical system 130, a second transmission system for transmitting the laser beam coming from the halving optical system to the test piece 182, the reflected beam detector 150, the transmitted beam detecting section 160, and the autofocus section 170.

The first transmission system is composed of the laser light source 111 for radiating the laser beam 119 for illumination, the attenuator 112 for adjusting the output intensity of the laser beam 119, the spatial filter 113, the deflection scan means 120 and 125 (including the beam expander 122, the half-wave plate 123, and the ultrasonic deflectors 121 and 126) for deflectively scanning the test piece with the laser beam 119 at high speeds, the cylindrical lens 114 for condensing the laser beam from the deflection scan means 120 and 125 in the X-axis direction, the beam splitter 115 for changing the progression direction of the laser beam 119 and to transmit part thereof, the power monitor 116 for detecting the laser beam transmitted through the beam splitter 115 and monitoring the output intensity of the laser beam 119 at the output side of the attenuator 112, the relay lens 117 on the side of the reflected light from the beam splitter 115, and the quarter-wave plate 118. The first transmission system thus constituted transmits the laser beam reflected by the beam splitter 115 to the halving optical system 130.

The halving optical system 130 for splitting the laser beam into two laser beams of P polarization and S polarization is composed of the polarizer 131 for splitting the incident laser beam 128 into two laser beams of P polarization and S polarization, the mirror 132*a* for changing the direction of one split laser beam 139, the wedge plate 133 composed of a wedge-shaped glass plate for altering the optical axis of the laser beam 139, the mirror 132*b* for changing the direction of the laser beam 139, the mirrors 132*c*, 132*d*, 132*e*, and 132*f* for changing the progression direction of the other split laser beam 138 and adjusting the transmission distance, and the polarizer 134 for synthesizing the split laser beams 138 and 139 into combined laser beams 129. The halving system 130 thus constituted transmits the synthesized laser beam 129 to the second transmission system.

The second transmission system is composed of the half mirror 141 for transmitting the laser beam 129 therethrough, the galvanomirror 142 and the mirror 143 for changing the direction of the laser beam to the X-axis direction instead of stage scan and for obtaining the image in a certain range, the telescope 144, the dichroic mirror 145 for changing the direction of the laser beam by reflecting the same, and the objective lens 146. The laser beam 149 is collected on the pattern surface of the test piece through the objective lens 146.

In the reflected beam detector 150, which is one of the image signal detecting means, the laser beam reflected from the test piece 182 returned in the optical path of the original laser beam enters the polarizer 152 after being reflected by the half mirror 141.

The reflected beam detector 150 is composed of the polarizer 152 for transmitting the P-polarized component of the reflected laser beam therethrough and reflecting the remaining component in the direction of the polarizer 155, the condenser lens 153 for condensing the P-polarized component transmitted through the polarizer 152 onto the detection surface of the reflected beam detector 154, the polarizer 155 for separating the S-polarized component from the light reflected from the polarizer 152, and the condenser lens 156 for condensing the separated S-polarized component onto the detection surface of the reflected beam detector 157.

The transmitted beam detecting section 160, which is another of the image signal detection means, is composed of the collector lens 161 for collecting the laser beam transmitted through the test piece 182, the polarizer 162 for transmitting the P-polarized component therethrough and reflecting the remaining portion in the direction of the polarizer 165, the condenser lens 163 for condensing the light transmitted through the polarizer 162 onto the detection surface of the transmitted beam detector 164, the transmitted beam detector 164, the polarizer 165 for separating the S-polarized light from the reflected light of the polarizer 162, the condenser lens 166 for condensing the separated S-polarized component onto the detection surface of the transmitted beam detector 167, and the transmitted beam detector 167.

The autofocus section 170 is composed of the autofocus light source 171 that uses a linear polarized laser beam such as He—Ne laser (wavelength 632.8 nm), the beam expander 172 for expanding the laser beam radiated from the autofocus light source 171, the beam splitter 173 for transmitting the laser beam therethrough radiated from the autofocus light source 171 and reflecting to the split detector 177 the reflected light from the test piece 182 and returned along the same optical path, the quarter-wave plate 178 for converting the linearly polarized light into the circularly polarized light, the compensating lens 174 for making the autofocus laser beam to focus on the same plane as the laser beam 149 after transmission through the objective lens 146, the mirror 175 for radiating along with the laser beam 129 transmitted through the dichroic mirror 145 onto the test piece 182 and reflecting the light reflected from the test piece 182 to the beam splitter 173, the collective lens 176 for collecting the light reflected from the beam splitter 173, the knife edge 179, and the split detector 177.

With further reference to FIG. 1, the image processing unit 191 is composed of the image data storage 191*b* for receiving the detect signals detected by the detectors from the light reflected from and transmitted through the test piece 182, generating images from the received detect signals, and sequentially storing the generated images, and storing image data of already inspected reference test pieces for use in the inspection based on the comparison between test pieces, the database storage 191*a* for storing corresponding image data to be obtained from the database when performing inspection by comparison between a test piece and a test piece database, the defect information storage 191*c* for storing the information about defects found by inspection, and the image processing controller 191*d* for collectively controlling the digital operations of the components of the image processing unit and interfacing with external devices.

The display 192 displays images, defect information, and so on, thereby informing the operator of the contents of detected defects through a display device such as CRT. The display is also used for editing the inputs from the data input section 193 to be described later.

The data input section 193 is used as man-machine interface for inputting data into the above-mentioned database and determining the contents of the display on the display 192 for example. Normally, a keyboard is used for the data input section.

The following describes the operation of the first embodiment of the present invention. The laser beam to be used preferably has a shorter ultraviolet wavelength from the viewpoint that the laser beam has a good focus, or the spot size on the test piece 182 must be as small as possible. However, in the wavelength band below 360 nm, the available lens materials are extremely limited, making it extremely difficult to fabricate a lens having a small aberration and, at the same time, difficult to fabricate the means for deflecting the laser beam. Consequently, a good result was obtained from the UV light of an Ar laser having a wavelength of 363.8 nm in the present embodiment.

The laser beam 119 radiated from the laser light source for illumination is deflected by the deflection scan means 120 and 125 in the Y direction and the deflected laser beam is split by the halving optical system 130 into P polarization and S polarization, which are radiated onto the test piece 182 held on the XY stage.

Figure 3:
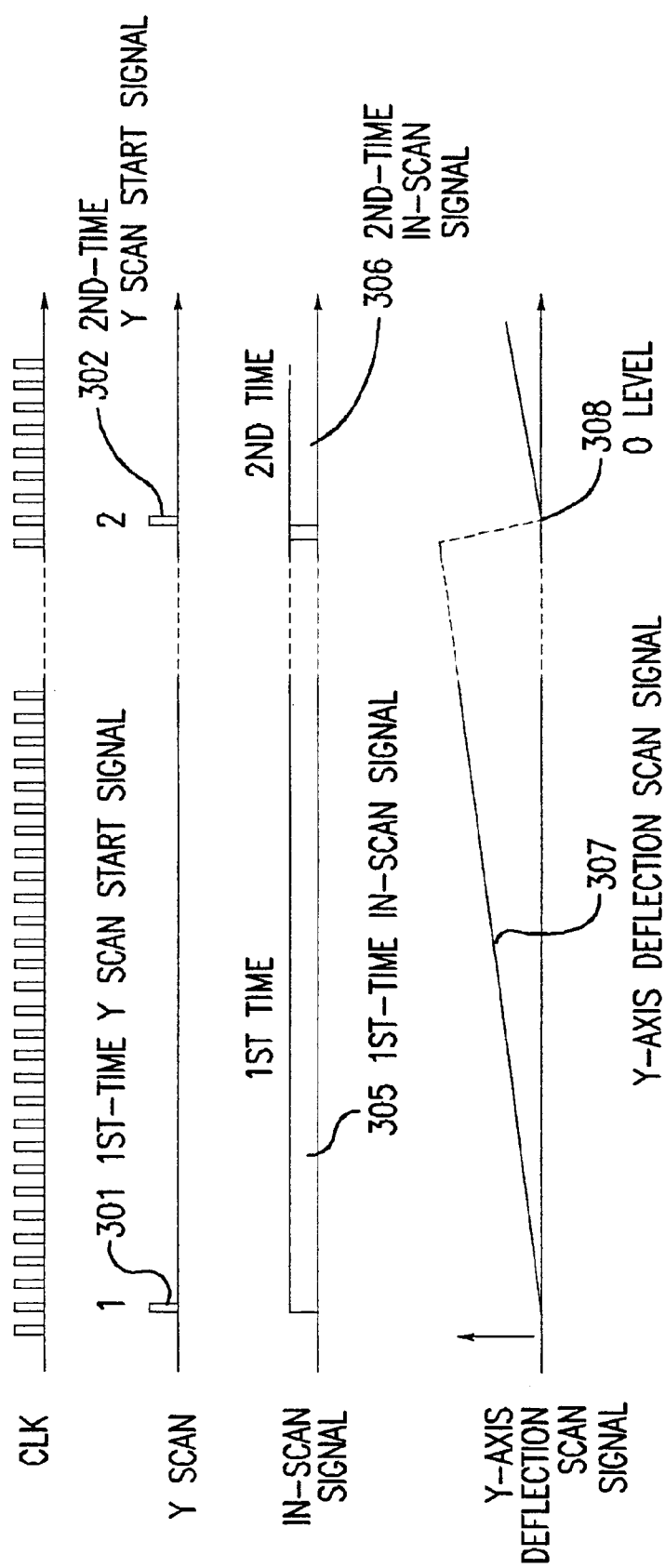
FIG. 3 is a timing chart of the deflection scan in the first embodiment of the invention.

With reference now to FIG. 3, a drive signal as indicated by the Y-axis deflection scan signal 307 is applied to the ultrasonic deflectors 121 and 126 of the deflection scan means 120 and 125. In synchronization with a clock pulse CLK, when the X stage comes to a predetermined position, the first-time Y scan start signal 301 is generated, from the first-time Y scan start signal 301, the first-time in-scan signal 305 is generated, and the drive signal indicated by the Y-axis deflection scan signal 307 is generated. When the first-time in-scan signal 305 is ON, the pattern surfaces in the scan area 1-1 and the scan area 1-2 of the test piece 182 are deflectively scanned with each of the two branched laser beams and the resultant image data is sampled.

When the first-time in-scan signal 305 goes OFF at the time the scan of the scan area 1 comes to an end, the Y-axis deflection scan signal 307 quickly returns to the 0 level 308 of the Y-axis deflection scan signal and is kept in the wait state until the second-time in-scan signal 306 is turned ON by the second-time Y scan start signal 302. The wait time is set as short as possible.

Figure 4A:
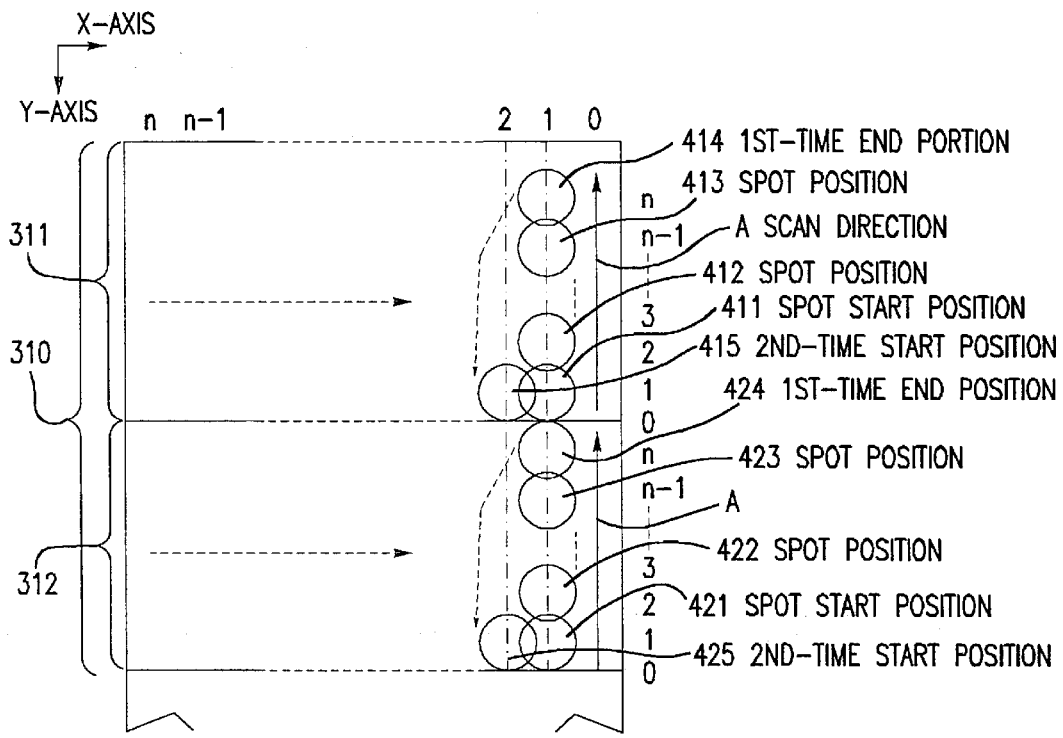
FIGS. 4(*a*) and 4(*b*) are diagrams illustrating a state of scan laser beam scanning on the test piece in the first embodiment of the invention.
Figure 4B:
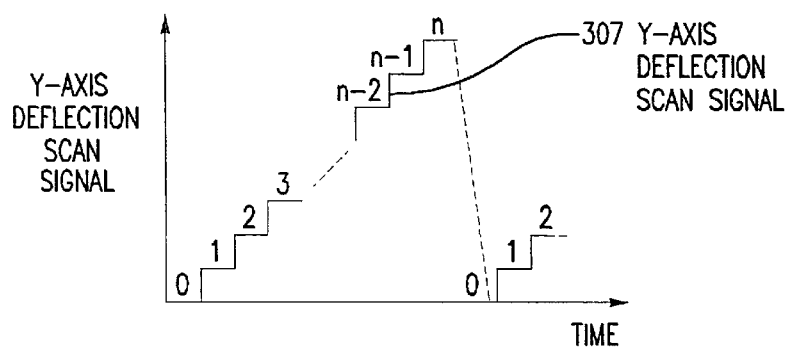

With reference to FIG. 4(a), the laser beam spot on the pattern surface of the test piece 182 moves as follows. Each of the two branched laser beams is initially at the positions 411 and 421 and moves in the direction of arrow A by the Y-axis deflection scan signal 307. The Y-axis scan signal 307 increases in steps (not linearly) at each spot position as shown in FIG. 4(b).

The first-time in-scan signal 305 goes OFF when the end positions 414 and 424 of the Y-axis scan of the area 1 are deflectively scanned with each laser beam. When the first-time in-scan signal 305 goes OFF, the Y-axis deflection scan signal 307 quickly returns to the 0 level 308 of the Y-axis deflection scan signal, so that each laser beam also returns to the radiation start position. When the XY stage moves in the X-axis direction, each laser is positioned at the second deflection scan start positions 415 and 425 and kept in the wait state until the second-time in-scan signal 306 is turned ON by the second-time Y scan start signal 302.

When the second-time Y in-scan signal 306 goes ON, the Y-axis deflection scan signal 307 is generated in the same manner as the first-time Y scan and the generated signal is applied to the deflector. Subsequently, the above-mentioned operation is repeatedly performed by the predetermined number of times on all areas of scan area 1.

Figure 5:
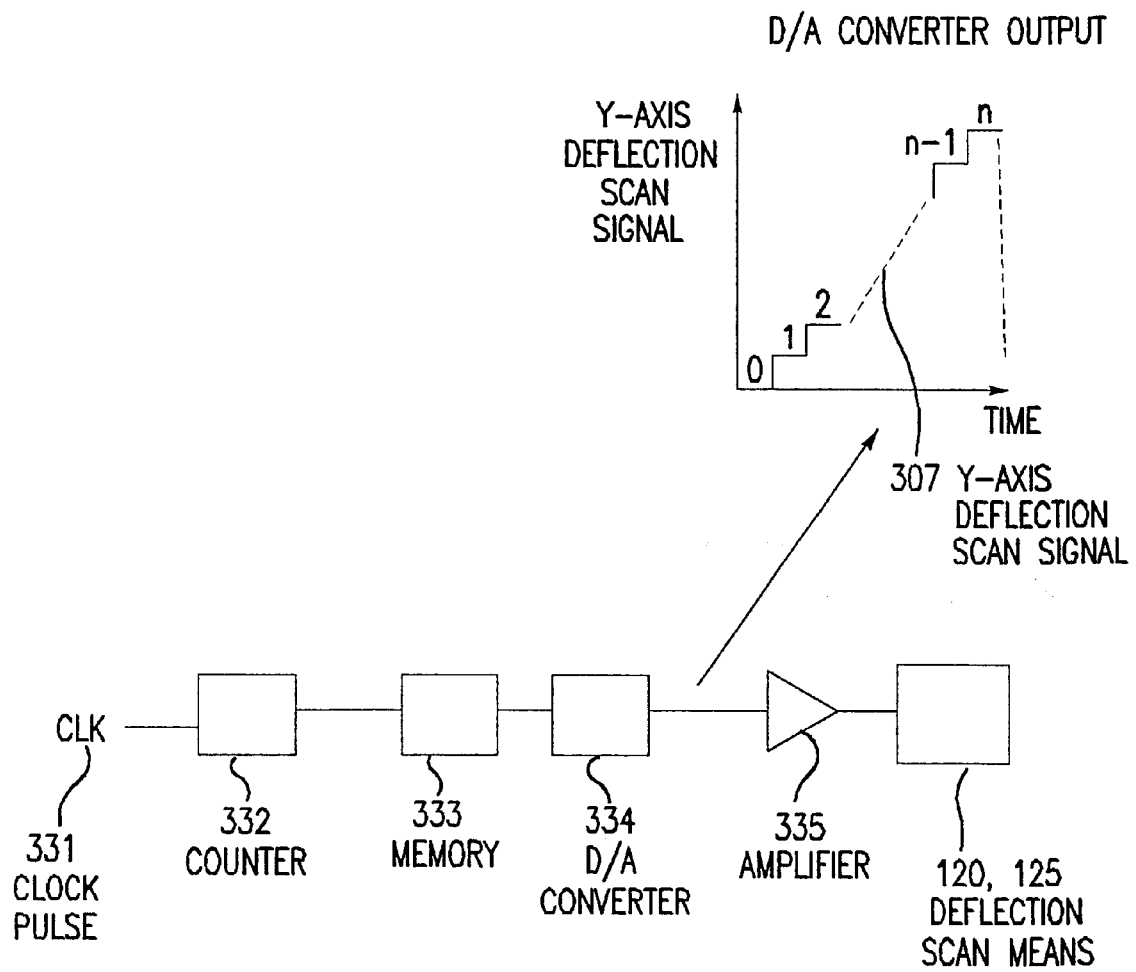
FIG. 5 is a block diagram illustrating operations of a circuit for generating the deflection scan signal in the first embodiment of the invention.

With reference to FIG. 5, the Y-axis deflection scan signal 307 to be inputted in the deflection scan means 120 and 125 is, as shown in FIG. 5, generated from the outputs of the counter 332 for counting the number of times the clock pulse CLK 331 is inputted, the memory 333 for performing the arithmetic operation to output an accumulated value every time the clock is counted by the predetermined number, the D/A converter 334 for converting the digital output of the memory 333 into an analog value, and the amplifier 335.

Figure 6A:
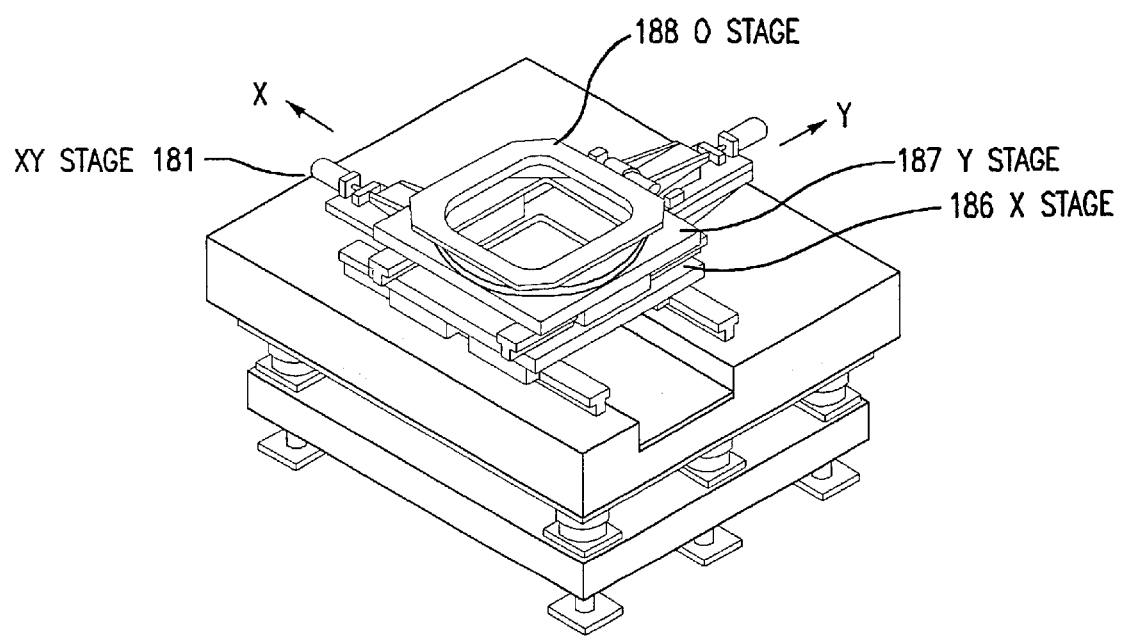
FIGS. 6(*a*) to 6(*c*) are schematic diagrams illustrating operations of the XY stage, in which FIG. 6(*a*) shows the perspective drawing illustrating the XY stage, FIG. 6(*b*) shows the operation of the first embodiment of the present invention and FIG. 6(*c*) shows the operation of a prior-art example.
Figure 6B:
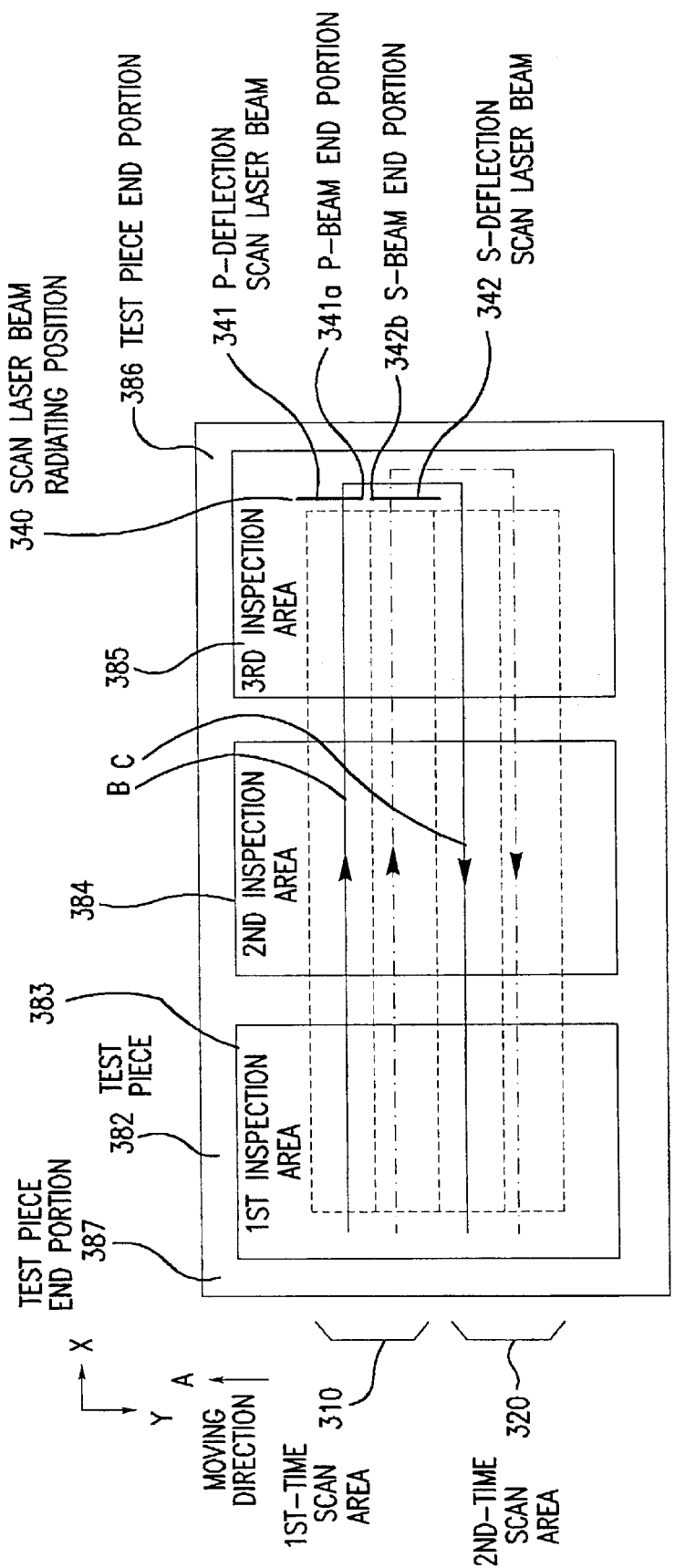

Referring to FIG. 6(b), the XY stage 181 carries the test piece 382 and moves in one direction along X-axis and, when the test piece end portion 387 reaches the scan laser beam radiation position 340, stops moving, upon which the X-axis feed for the first-time scan area 310 shown in FIG. 6(b) comes to an end.

The position 340 is a fixed position. The laser beam is branched into two at this position, which are scanned in Y direction to provide the P-polarized scan laser beam 341 and the S-polarized scan laser beam 342 for example. It should be noted that, for convenience of description, an end 341a of the laser beam 341 and an end 342b of the laser beam 342 are shown with a space in between; actually, however, the scan width of each laser beam is set such that both the laser beams 341 and 342 overlap with each other.

Next, when the XY stage 181 has been fed two steps in Y direction (the direction indicated by arrow A), the XY stage 181 is fed in X-axis direction, which is perpendicular to the Y direction, upon which the second X-axis feed of the scan area 320 starts. When the test piece end 387 subject to inspection has reached the scan laser beam radiation position 340, the XY stages stops.

Although not shown in FIG. 6(b), if there are multiple scan areas such as a third scan area and a fourth scan area, the X-axis scan and the Y-axis step feed are repeated such that all the scan areas on the test piece are scanned with the scan laser beams 341 and 342.

Meanwhile, the output intensity of the laser beam 119 is monitored by the power monitor 116. Using a detect signal of this power monitor 116, the attenuator 112 is controlled by a laser power controller (not shown) to maintain the output intensity of the laser beam 119 at a constant level.

The above-mentioned operations are performed in cooperation with the operations of other components under the control of the system controller 190.

Figure 6C:
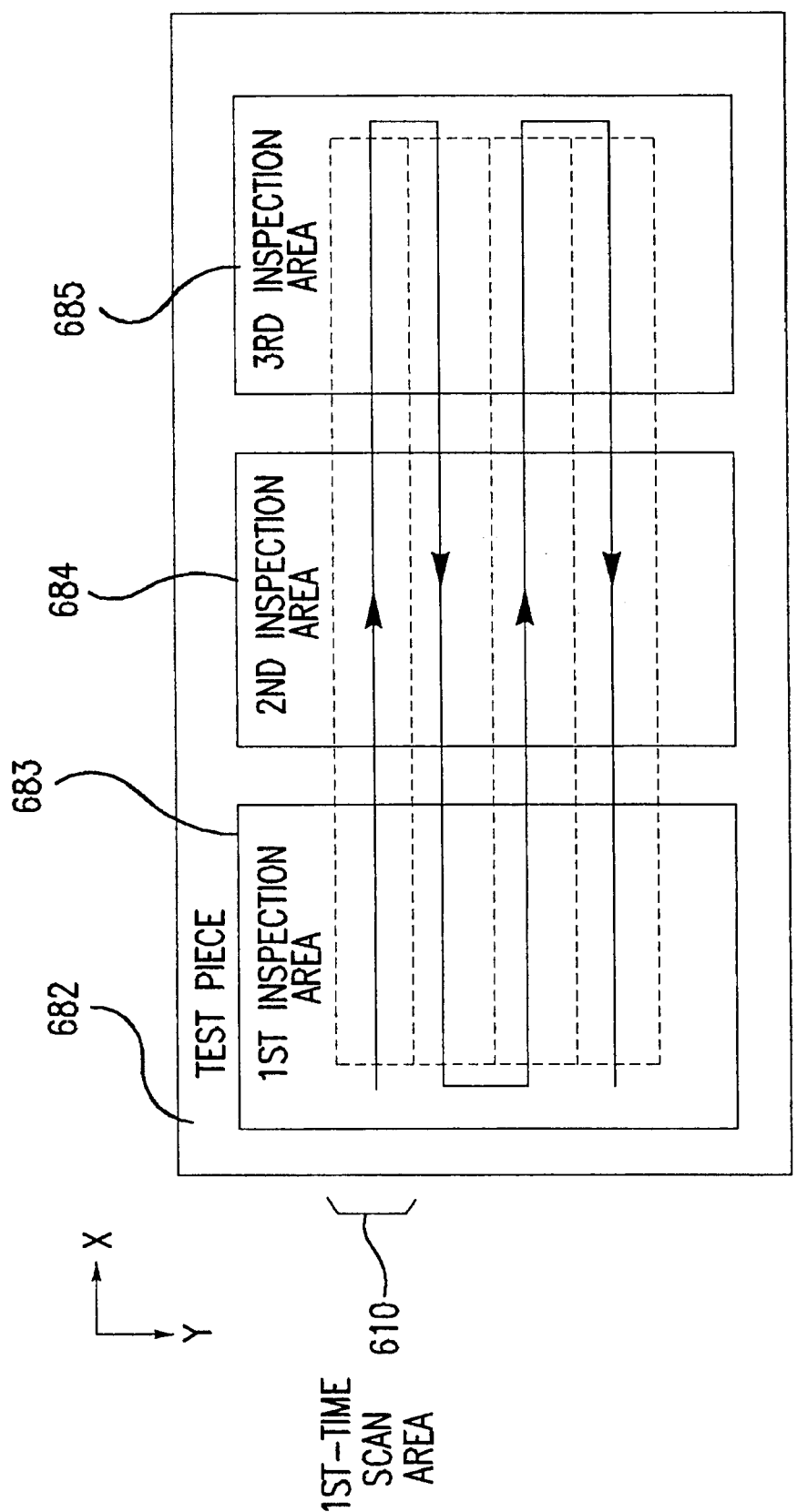

Referring to FIG. 6(c), in the prior-art example, the two split laser beams as used in the present embodiment are not used. Therefore, the first-time scan area is half the first-time scan area of the present embodiment in scan width, resulting in the same X-axis direction as the present embodiment but a single-step feed in Y direction. Consequently, as compared with the present invention, the time for inspecting the test piece is approximately doubled. In other words, the present invention can reduce the inspection time to a half of the prior-art example, providing a significant advantage.

The following describes in detail the operation of the optical system 110 with reference to FIG. 2. The laser beam 119 radiated from the laser light source 111 using UV-Ar laser is adjusted in output intensity by the attenuator 112 and the adjusted laser beam is transmitted through the spatial filter 113 to be deflectively scanned in Y-axis direction on the inspection images (as shown in FIG. 6(b)) by the deflection scan means composed of a pair of the ultrasonic deflector 121 and the ultrasonic deflector 126. The laser beam outputted from the ultrasonic deflector 126 is focused in the X-axis direction through the cylindrical lens 114. In the Y-axis direction, the laser is focused, as with the cylindrical lens 114, to the same focus position by the condensing action of the ultrasonic deflector 126 itself. Then, the laser is transmitted through the relay lens 117 and the quarter-wave plate 118 via the beam splitter 115 to be branched by the halving optical system 130.

The laser beam transmitted through the beam splitter 115 is received by the power monitor 116, by which variations in the laser beam intensity are monitored.

The laser beam entering the halving optical system 130 is put in the circularly polarized state by the quarter-wave plate 118 to be branched into two laser beams of P polarization and S polarization. One of the branched laser beams, or the laser beam 139 is altered in the tilt of the optical axis thereof through the mirror 132a to be entered in the polarizer 134 via the mirror 132b.

The other laser beam 138 is entered in the polarizer 134 through the transmission distance adjusting mirrors 132c, 132d, 132e, and 132f. The polarizer 134 synthesizes the laser beams 138 and 139 branched by the polarizer 131. The resultant synthesized laser beam consists of P polarization and S polarization.

These laser beams have a slightly different light axis direction from each other. This difference in the direction of the axes is adjusted by adjusting the tilt of the wedge plate 133 such that these laser beams are separated from each other by a width equivalent to the scan area width shown in FIG. 6(b). In the state in which the laser beams are focused on the surface of the test piece, a positional change results from the tilt of the wedge plate 133 is about 0.05 $\mu$m on the test piece surface, an extremely precise adjustment. Thus, in spite of having only one system as a laser beam scanning means in the Y-axis direction, two areas on the test piece 182 can be simultaneously scanned and the parallel processing can be performed.

The laser beam 129 outputted from the halving optical system 130 passes through the half mirror 141 and is reflected from the galvanomirror 142 and the mirror 143 to enter the telescope 144. The galvanomirror 142 changes the direction of the laser beam to the X-axis direction instead of stage scan to obtain an image of a certain area. In inspecting the patterns of reticles, as described later, the XY stage 181 mounting reticles is moved to obtain an image.

The laser beam outputted from the telescope 144 is reflected by the dichroic mirror 145 to be mixed with the autofocusing laser beam transmitted through the dichroic mirror 145, which will be described later. The resultant laser beam enters the objective lens 146.

The telescope 144 can alter the size of the scan spot and scan area of the laser beam on the test piece 182, so that the minimum value of detectable defects can be selected. It is also possible to design the lens system of the telescope 144 such that the length of the scan range is increased in proportion to the scan spot size. The laser beam coming from the telescope 144 is focused onto the surface of the test piece 182 through the objective lens 146.

The laser beam 119 radiated from the laser light source 111 onto the test piece 182 is partially reflected from the pattern surface of the test piece 182 to return along the original laser beam optical path and is further reflected from the half mirror 141 to go in the direction of the polarizer 152 of the reflected beam detector 152. This reflected laser beam enters the polarizer 152 and the P polarization transmitted through the polarizer 152 is condensed by the condenser lens 153 to be received by the reflected beam detector 154. On the other hand, as for the beam reflected from the polarizer 152, the S polarization transmitted through the polarizer 155 enters the condenser lens 156 to be received by the reflected beam detector 157.

The laser beam transmitted through the test piece 182 is collected by the collector lens 161 and P polarization is transmitted through the polarizer 162 and condensed by the condenser lens 163 to be received by the transmitted beam detector 164. On the other hand, as for the laser beam reflected from the polarizer 162, the S polarization is reflected by the polarizer 165 and enters the condenser lens 166 to be received by the transmitted beam detector 167.

The laser beam radiated from the autofocusing light source 171 that uses He-Ne laser (linear polarized laser of wavelength 632.8 nm) in the autofocus section 170 passes through beam expander 172 to obtain the desired beam size, beam splitter 173, quarter wave plate 178, compensating lens 174, mirror 175 to alter the tilt of light path, and dichroic mirror 145, so that the autofocusing laser beam is focused onto the surface of the test piece 182 through objective lens 146 and the laser beam is reflected by the surface of the test piece 182.

The reflected beam returns in the direction opposite to the direction of incidence to the test piece 182, transmits through the dichroic mirror 145, reflected by the mirror 175 to change direction, reflected again by the beam splitter 173 by the action of the quarter-wave plate 178, collected by the collective lens 176, and enters the split detector 177.

In front of the split detector 177 is a light cutting plate, that is to say, knife edge 179 is located so as to cut off half of the light.

The knife edge 179 is aligned so that equal quantities of light enter both detectors of split detector 177 only when the test piece 182 is at such position that the reflected He-Ne laser beam is focused on the surface of the split detector 177. When the height of the surface of the test piece 182 changes, the focus position of the reflected laser beam changes and light quantity entering each detector of the split detector 177 becomes unbalanced because part of reflected light is cut off by the knife edge 179. By taking out the difference between detectors as a detect signal and altering the up-down position of the objective lens 146 through servo mechanism (not shown) that drives the objective lens 146, feed-back position control is performed so that the focus of the laser beam from the laser light source 111 for illumination and the focus of the laser beam from the laser light source 171 for autofocusing are matched to each other on the test piece surface.

The present embodiment has a laser beam for autofocusing that has a wavelength band different from that of the laser light source for pattern visual checking for the following reason. In the inspection of high-precision patterns to which the present invention is to be applied, it is required to focus the laser spot size on the surface of the test piece 182 as small as the order of the wavelength. To do so, the numerical aparture (NA) of the objective lens 146 must be made fairly large. The objective lens having a high NA is inevitably shallow in focal depth. In the present embodiment, the required accuracy of autofocusing is 0.05 $\mu$m. Key to achieving such a high accuracy is to clearly detect the signal difference in the split detector 177, which is the of autofocusing detector. Since only a semiconductor device is available for the practical split detector 177, it is not advantageous to use UV light because of the low UV sensitivity of reception by the semiconductor device. Therefore, the present embodiment uses the He—Ne laser in a wavelength band wherein the semiconductor split detector 177 has greater sensitivity.

Next, the following describes the operation of the XY stage 181 during inspection with reference to FIG. 6. The test piece 182 is set on the XY stage 181 with 3-degrees, that is to say, X, Y and θ directions, of freedom. In this embodiment, XY stage 181 has a stacked structure of the X stage 186, the Y stage 187 and the θ stage 188 in this order and moves in the X direction when the inspection images are obtained.

The test piece 182 is set precisely and held on the stage 181 by a transfer mechanism (not shown). Next, the θ stage 188 is operated and an alignment is performed. By aligning with the θ stage, a more precise operation is maintained than by aligning with only an XY interpolation operation.

The operation of the XY stage 181 during inspection is as illustrated below. First of all, the X stage 186 is automatically fed with a constant velocity and, until the image obtaining points pass through the inspection area 383, 384, 385, the Y stage 187 maintains register and does not perform the interpolating operation. The image obtaining points pass through the inspection area 385 and when the X stage 186 stops, the Y stage 187 is stepfed and the X stage is automatically fed in the opposite direction with a constant velocity.

While the X stage 186 is fed with the constant velocity, the UV-Ar laser beams repeatedly scan on the inspection area 383, 384, 385 in the Y-axis direction by the ultrasonic deflector 121, 126 and the reflected light and transmitted light are detected by the above-mentioned reflected beam detector 150 or transmitted beam detecting section 160.

Each table is driven by a mechanism (not shown) that converts the rotary movement of an AC servo motor into linear movement by a ball screw.

In closing, the following describes the signal processing method. The image processing unit 191 receives the detect signals from the detectors of the beams transmitted through and reflected from the test piece 182, generates image data from the received detect data, and stores the generated image data in the image data storage 191b. Normally in the case of inspecting defects of shapes, size and so on, transmitted light is only used and in the case of inspecting for foreign particles, the reflected light is only used.

In the case where a plurality of the same circuit patterns are formed on the same test piece and the piece-to-piece inspection method is adopted, when a comparison is made between the image data taken out by the detector and the image data of a test piece having the same features already inspected and stored in the image data storage 191b and, if a mismatch is found, the position of the detected defect, defect image data, and reference data are stored as defect information into the defect information storage 191c.

On the other hand, for test piece-to-database inspection, a comparison is made between the image data of the piece inspected and the corresponding image information stored in the database storage 191b to detect a defect. The detected defect is stored as defect information.

The display 192 shows the image, defect information, and so on to inform the operator of the contents of the detected defect.

Figure 7:
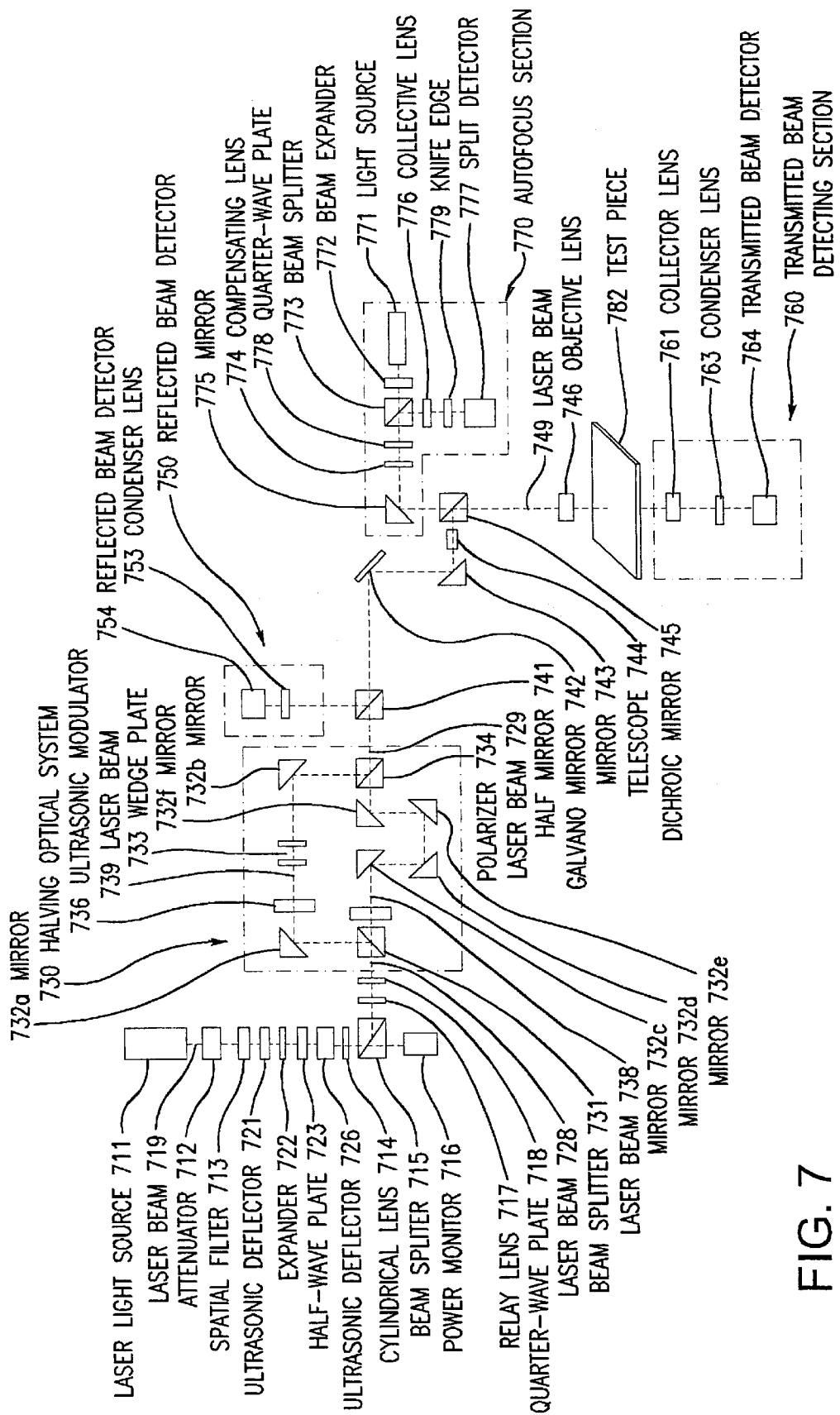
FIG. 7 is a detailed block diagram illustrating an optical system of an apparatus for inspecting high-precision patterns, practiced as the second embodiment of the invention.

The following describes a second embodiment of the present invention with reference to drawings. In FIG. 7, reference numeral 711 denotes a laser light source, reference numeral 712 an attenuator, reference numeral 713 a spatial filter, reference numeral 714 a cylindrical lens, reference numeral 715 a beam splitter, reference numeral 716 a power monitor, reference numeral 717 a relay lens, reference numeral 718 a quarter-wave plate, reference numeral 719 a laser beam, reference numeral 721 an ultrasonic deflector, reference numeral 722 a beam expander, reference numeral 723 a half-wave plate, reference numerals 728 and 729 laser beams, reference numeral 730 a halving optical system, reference numeral 731 a beam splitter, reference numerals 732a, 732b, 732c, 732d, 732e, and 732f mirrors, reference numeral 734 a prism, reference numerals 735 and 736 ultrasonic modulators, reference numerals 738 and 739 laser beams, reference numeral 741 a half mirror, reference numeral 742 a galvanomirror, reference numeral 743 a mirror, reference numeral 744 a telescope, reference numeral 745 a dichroic mirror, reference numeral 746 an objective lens, reference numeral 749 a laser beam, reference numeral 750 a reflected beam detector, reference numeral 753 a condenser lens, reference numeral 754 a reflected beam detector, reference numeral 760 a transmitted beam detecting section, reference numeral 761 a collector lens, reference numeral 763 a condenser lens, reference numeral 764 a transmitted beam detector, reference numeral 770 an autofocus section, reference numeral 771 a light source, reference numeral 772 a beam expander, reference numeral 773 a beam splitter, reference numeral 774 a compensating lens, reference numeral 775 a mirror, reference numeral 776 a collective lens, reference numeral 777 a split detector, reference numeral 778 a quarter-wave plate, and reference numeral 782 a test piece.

Referring to FIG. 7, the second embodiment differs from the first embodiment in the halving optical system 730. Namely, the polarizer 131 of the halving optical system 130 in the first embodiment shown in FIG. 2 is replaced by the beam splitter 731 and the polarizer 134 is replaced by the prism 734 that synthesizes the branched laser beams 738 and 739 into laser beam 729. Further, the ultrasonic modulators 735 and 736 are arranged in the optical paths of the branched laser beams 738 and 739.

Next, the reflected beam detector 750 does not require the polarizers 152 and 155 shown in FIG. 2 and is composed of a pair of the condenser lens 753 and the reflected beam detector 754. The transmitted beam detecting section 760 does not require the polarizers 162 and 165 is composed of only the collector lens 761, the condenser lens 763, and the transmitted beam detector 764. The other components are the same as those of FIG. 2 and the description of these components will be omitted.

The following describes the operation of the second embodiment mainly in the differences from the first embodiment. Referring to FIG. 7, the laser beam radiated from the laser light source 711 changes its direction through the beam splitter 715 to enter the halving optical system 730.

The laser beam entered in the halving optical system 730 is split by the beam splitter 731 into two laser beams 738 and 739.

The laser beam 738 and the laser beam 739 are analog-modulated by the ultrasonic modulator 735 and the ultrasonic modulator 736 respectively to be changed in the intensity of light. This analog modulation is performed in a time division manner, which will be described later.

Figure 8:
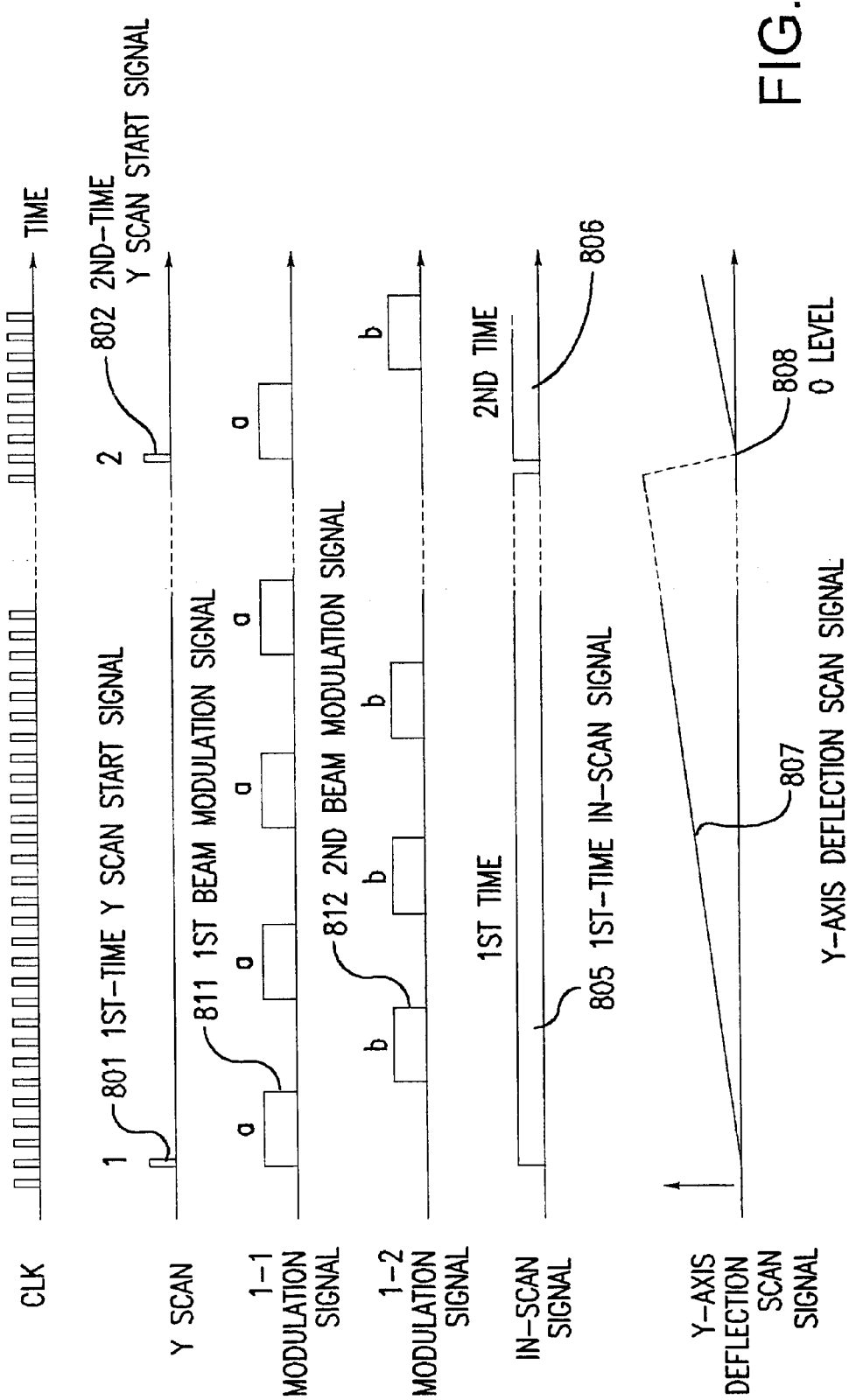
FIG. 8 is a timing chart of the deflection scan of the second embodiment.

FIG. 8 is a timing chart of the deflection scan of the second embodiment. In the figure, reference numeral 801 denotes a first-time Y scan start signal, reference numeral 802 a second-time Y scan start signal, reference numeral 805 a first-time in-scan signal, reference numeral 806 a second-time in-scan signal, reference numeral 807 a Y-axis deflection scan signal, reference numeral 808 the 0 level of Y-axis deflection scan signal, reference numeral 811 a first beam modulation signal (a), and reference numeral 812 a second beam modulation signal (b).

Corresponding to two branched scan areas of the first-time scan area 1, the ultrasonic modulator 735 outputs the first beam modulation signal 811 to the first beam scan area using the timing of a 1—1 modulation signal a and the ultrasonic modulator 736 outputs the second beam modulation signal 812 to the second beam scan area using the timing of a 1-2 modulation signal b to perform a modulating operation.

The laser beam 739 of FIG. 7 is altered in the tilt of its optical axis by the wedge plate 733. As with the first embodiment, this tilt is adjusted in units of the scan area width of the test piece 382 shown in FIG. 6(*b*).

Both the analog-modulated laser beams are synthesized by the synthesizing prism 734 to be radiated onto the test piece 782 as described with reference to the first embodiment.

Figure 9A:
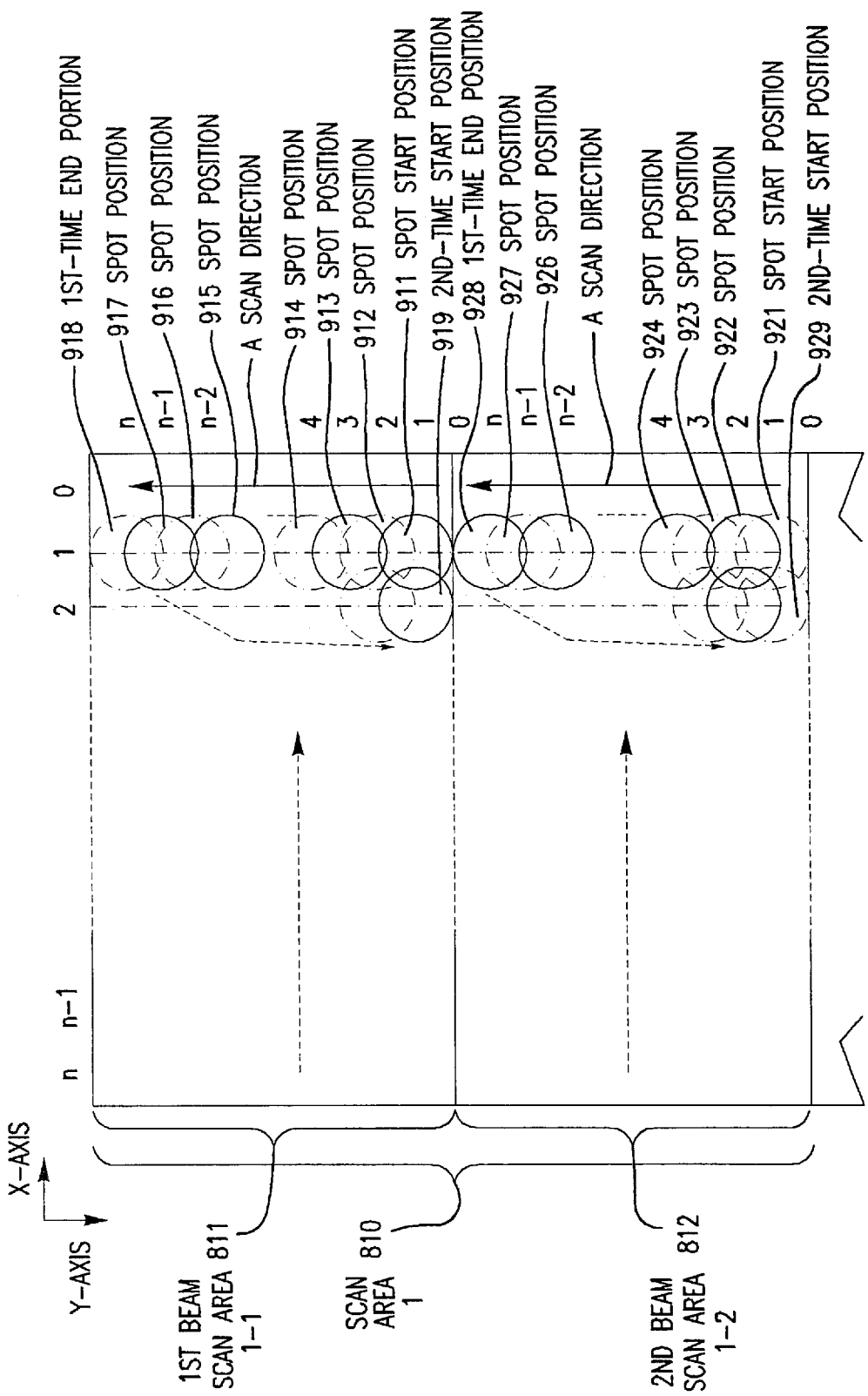
FIGS. 9(*a*) and 9(*b*) are diagrams illustrating a state of scan laser beam scanning on the test piece in the second embodiment of the invention, in which FIG. 9(*a*) is a schematic diagram of the scan state and FIG. 9(*b*) is a graph showing a relationship between the Y-axis deflection scan signal and the elapsed time.
Figure 9B:
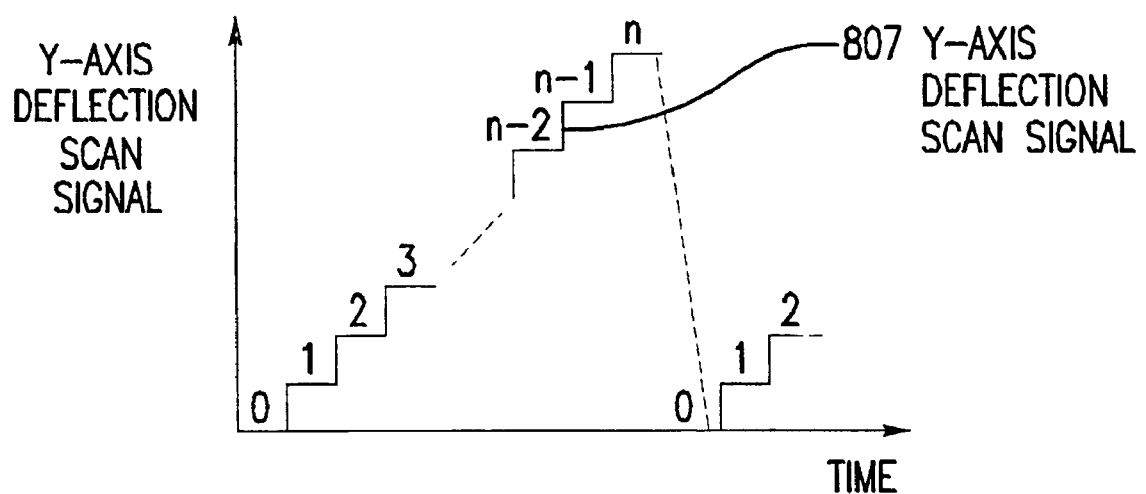
Figure 10:
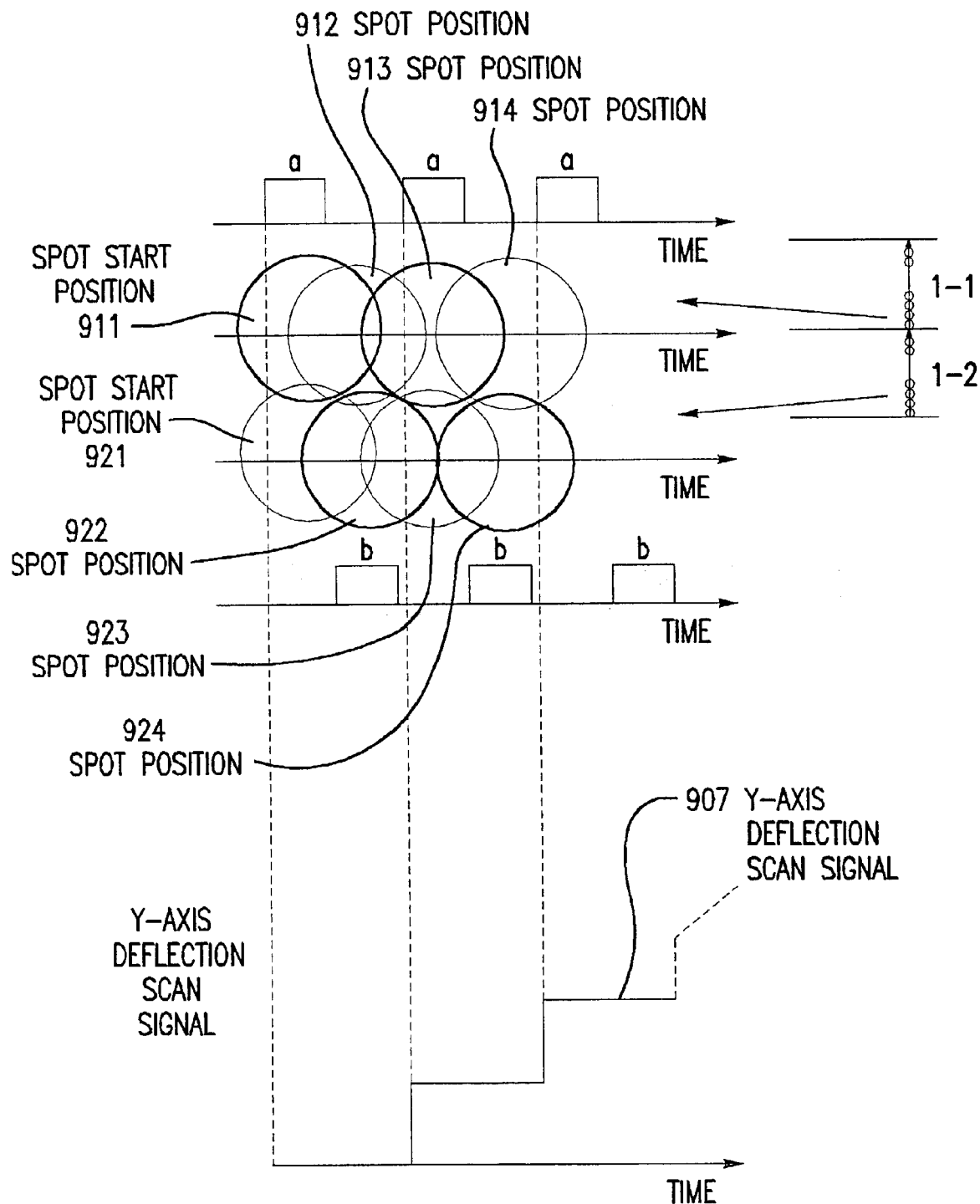
FIG. 10 is a schematic diagram illustrating in detail the relationship between scan areas, the modulation signals, and the Y-axis deflection scan signal of the second embodiment.

The following describes the operation of the scan laser beam on the surface of the test piece 782 with reference to FIGS. 8, 9, and 10.

FIG. 9 is a diagram illustrates a state of scan laser beam scanning on the test piece in the second embodiment of the invention. In the figure, FIG. 9(*a*) is a schematic diagram of the scan state and FIG. 9(*b*) is a graph showing a relationship between the Y-axis deflection scan signal and the elapsed time. Reference numeral 810 denotes a scan area 1, reference numeral 811 a first beam scan area 1-1, reference numeral 812 a second beam scan area 1-2, reference numeral 911 a first beam spot start position, reference numerals 912, 913, 914, 915, 916, and 917 spot positions, reference numeral 918 first-time end position, reference numeral 919 a second-time start position, reference numeral 921 a second beam spot start position, reference numerals 922, 923, 924, 925, 926, and 927 spot positions, reference numeral 928 a first-time end position, and reference numeral 929 a second-time start position.

The two branched laser beams are initially at the spot positions 911 and 921 and then moved in the direction of arrow A by the Y-axis deflection scan signal 807. Meanwhile, the two branched laser beams are modulated alternately as described above, so that the strong laser beam and the weak laser beam appear alternately on the scan areas 1-1 and 1-2 of the pattern surface of the test piece 782.

In the figure, thick-line circles 911, 913, 915, 917, and 919 denote strong laser beams and thin-line circles 912, 914, 916, and 918 denote laser beams of which intensity is nearly zero.

For the convenience of description, the laser beam on the side of scan area 1-1 is P polarization, while the laser beam on the side of scan area 1-2 is S polarization. When the laser beam of P polarization corresponding to the scan area 1-1 is at one of the positions 911, 913, 915, and 917, or the first-time-axis in-scan signal 805 of FIG. 8 is ON and the 1-1 modulation signal a of the first beam modulation signal 811 is ON, the reflected beam detected by the reflected beam detector 750 of FIG. 7 provides the reflected beam detect signal corresponding to the scan area 1-1 of the test piece 782.

At this moment, the reflected beam of the S polarization laser beam is also detected from the scan area 1-2 by the reflected beam detector 750. Since this laser beam is of intensity nearly equal to zero corresponding to the thin-line circles 921, 923, 927 and so on, the reflected beam detect signal of this laser beam is distinguished from the strong reflected beam detect signal coming from the scan area 1-1.

When the S-polarization laser beam corresponding to the scan area 1-2 is at one of positions 922, 924, 926, and 928, or the first-time-axis in-scan signal 807 of FIG. 8 is ON the 1-2 modulation signal b of the second beam modulation signal 812 is ON, the reflected beam detected by the reflected beam detector 750 provides the reflected beam detect signal corresponding to the scan area 1-2 of the test piece 782. At the same time, the reflected beam of the P-polarization laser beam is also detected from the scan area 1-1 by the reflected beam detector 750. Since this laser beam has an intensity nearly equal to zero corresponding to thin-line circles 912, 914, 916, 918 and so on, this reflected beam is distinguished from the strong reflected beam detect signal coming from the scan area 1-2. As described above, the second embodiment uses the reflected beam detecting means that synchronizes with the modulation signal and does not require the separating means for separating P polarization from S polarization in the reflected beam detector 29 in the first embodiment, enabling the simultaneous detection of the branched laser beams at two positions regardless of the laser beam polarized state.

Also, the second embodiment is applicable to an optical system that branches the laser beam into two by use of polarization, in which the detection of better S/N ratio is possible.

FIG. 10 is a diagram illustrating in detail the relationship between the modulation signals a and b, the scan areas 1-1 and 1-2, and the Y-axis deflection scan signal 907.

The beam transmitted through the test piece 782 is detected by the transmitted beam detector 764 through the collector lens 761 and the condenser lens 763 of the transmitted beam detecting section 760. The method in which the transmitted beam is detected is the same as the method in which the reflected beam detect signal is detected and therefore the description will be omitted.

The other operations are the same as those described with reference to the first embodiment and therefore the description will be omitted.

Figure 11:
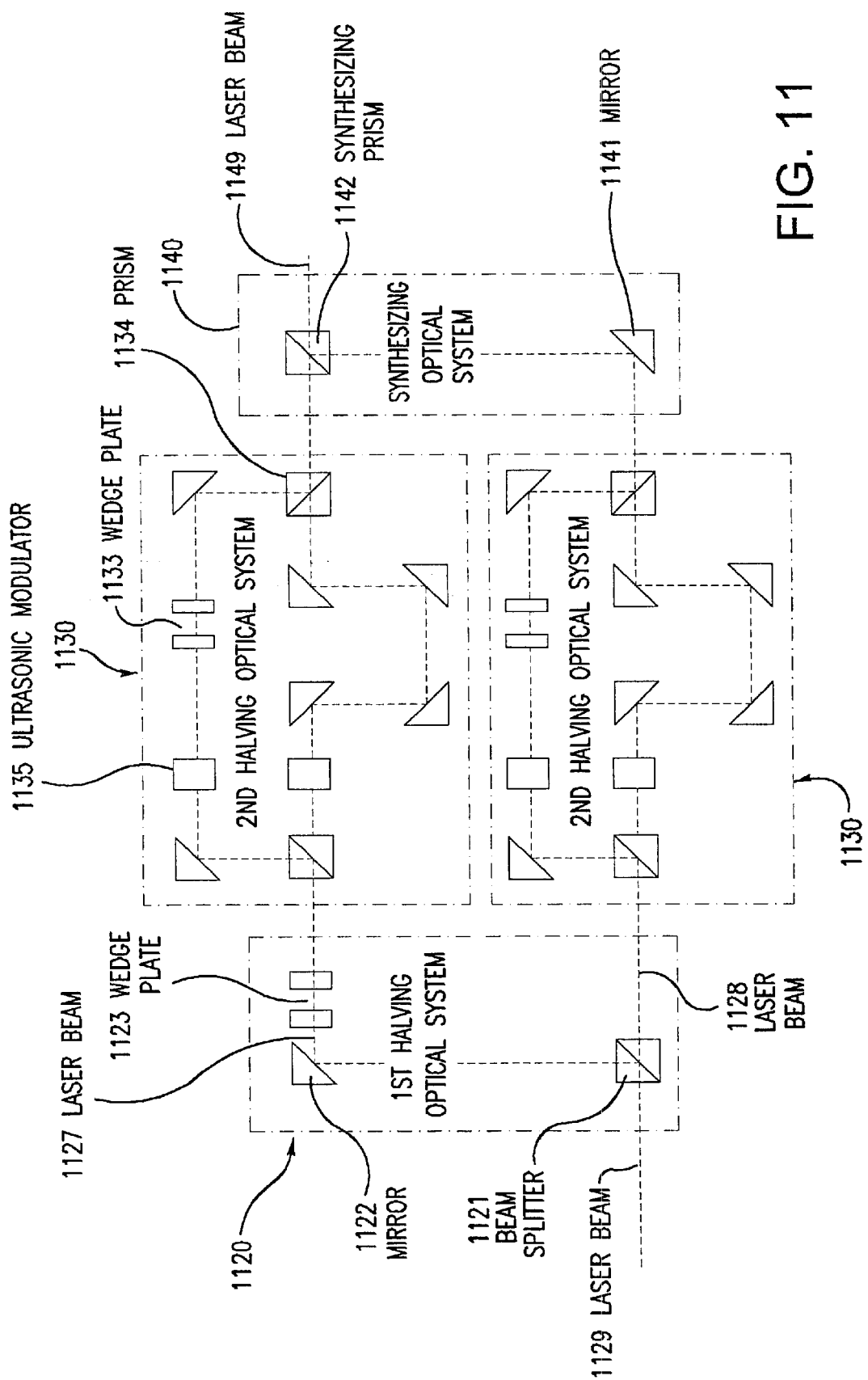
FIG. 11 is a general block diagram illustrating an optical system for quartering the laser beam of an apparatus for inspecting high-precision patterns, practiced as the third embodiment of the invention.

The following describes a third embodiment of the invention with reference to FIG. 11. FIG. 11 is a block diagram illustrating an optical system for quartering the laser beam of an apparatus for visually inspecting high-precision patterns, practiced as the third embodiment of the invention. In the figure, reference numeral 1120 denotes a first halving optical system, reference numeral 1121 a beam splitter, reference numeral 1122 a mirror, reference numeral 1123 a wedge plate, reference numerals 1127, 1128, and 1129 laser beams, reference numeral 1130 a second halving optical system, reference numeral 1133 a wedge plate, reference numeral 1135 an ultrasonic modulator, reference numeral 1140 a synthesizing optical system, reference numeral 1141 a mirror, reference numeral 1142 a synthesizing prism, and reference numeral 1149 a laser beam.

The third embodiment comprises the first halving optical system 1120 composed of the beam splitter 1121, the mirror 1122, and the wedge plate 1123, two sets of the second halving optical systems the same as that described with reference to the second embodiment, and the synthesizing optical system 1140 for synthesizing two branched laser beams composed of the mirror 1141 and the synthesizing prism 1142.

Figure 12:
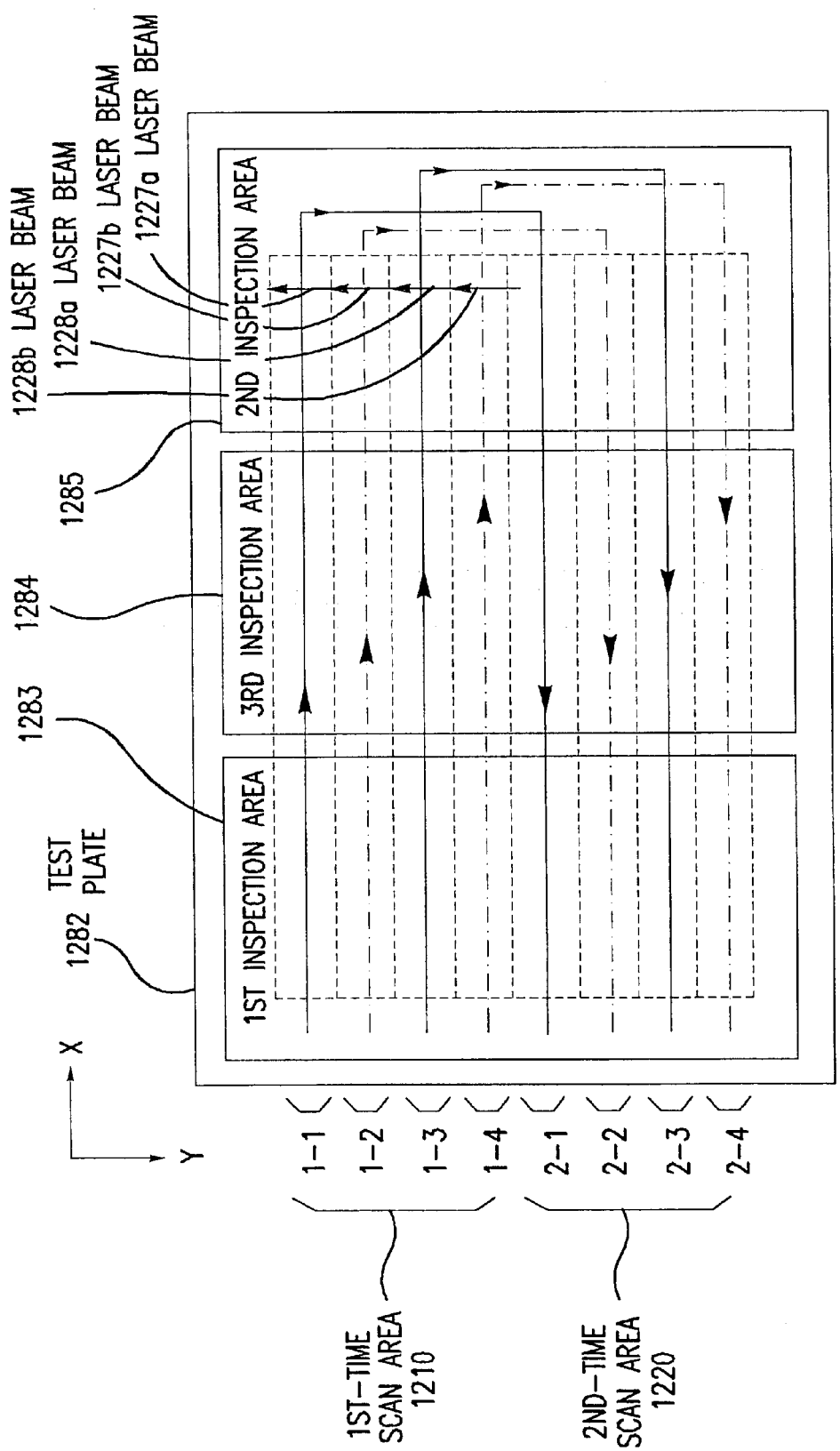
FIG. 12 is a schematic diagram illustrating the operation of the XY stage practiced as the third embodiment of the invention.

The following describes the operation of the third embodiment. Referring to FIG. 11, the laser beam 1129 is branched into two by the first halving optical system 1120. The branched laser beams 1127 and 1128 enter the different second halving optical systems 1130 to be further branched into two. Namely, the laser beam 1129 is eventually branched into four, the four branched laser beams are processed separately, and the processed laser beams are synthesized by the synthesizing prism 1142 into the laser beam 1149 to be radiated onto the test piece 1282 (FIG. 12).

The following describes the states of the branched laser beams. The laser beam 1129 is branched into two by the first halving optical system 1120. The optical path of one laser beam 1127 is tilted by the wedge plate 1123 toward the optical path of the other laser beam 1128 to change the position between both the laser beams, which enter the different second halving optical systems 1130. The amount of the positional change between the two laser beams is adjusted to a separated width such that the laser beam 1127 can scan the scan area 1-1 of the test piece 1282 and the other laser beam 1128 can scan the scan area 1-3 of the test piece 1282.

The tilted laser beam 1127 is further branched into two by the second halving optical system 1130. At this moment, one of the branched laser beams is separated from the other by the area width equivalent to the scan area 1-1 by the wedge plate 1133. The position between the two laser beams is determined by adjusting the tilt such that the scan area 1-2 can be scanned. Consequently, the laser beam 1127 is branched into two, one of them scanning the scan area 1-1 and other scanning the scan area 1-2.

As for the other laser beam 1128 coming from the first halving optical system, the mutual position is adjusted by the wedge plate 1133 like the laser beam 1127 and is radiated to the scan area 1-3 and the scan area 1-4. Namely, the four branched laser beams are radiated to the four divided scan areas 1-1, 1-2, 1-3, and 1-4 of the scan area 1 respectively.

The four branched laser beams are synthesized by the prism 1134 of the second halving optical system 1130 and the synthesizing optical system 1140 into the laser beam 1149 to be radiated onto the test piece 1282. A total of four optical paths in the halving optical systems are analog-modulated by the ultrasonic moudulators 1135 in a time division manner using different timing for light intensity changes.

FIG. 12 is a schematic diagram illustrating the operation of the XY stage practiced as the third embodiment of the invention. In the figure, reference numeral 1210 denotes a first-time scan area, reference numeral 1220 a second-time scan area, reference numeral 1227a a first laser beam, reference numeral 1227b a second laser beam, reference numeral 1228a a third laser beam, reference numeral 1228b a fourth laser beam, reference numeral 1282 a test piece, reference numeral 1283 a first inspection area, reference numeral 1284 a second inspection area, and reference numeral 1285 a third inspection area.

The scan area 1-1 is scanned with the laser beam 1227a, one of the laser beams resulting from branching the laser beam 1127, and the scan area 1-2 is scanned with the other laser beam 1227b. The scan area 1-3 is scanned with the laser beam 1128a, one of the laser beams resulting from branching the laser beam 1128 and the scan area 1-4 is scanned with the other laser beam 1128b.

It will be apparent that the same effect as above can be obtained if the correspondence between the branched laser beams 1127 and 1128 and the scan areas is reverse to the above-mentioned relationship.

As described above, the laser beam is split into four to be radiated onto the surface of the test piece 1282. These laser beams are analog-modulated as described above, which is illustrated in FIGS. 13 and 14.

Figure 13:
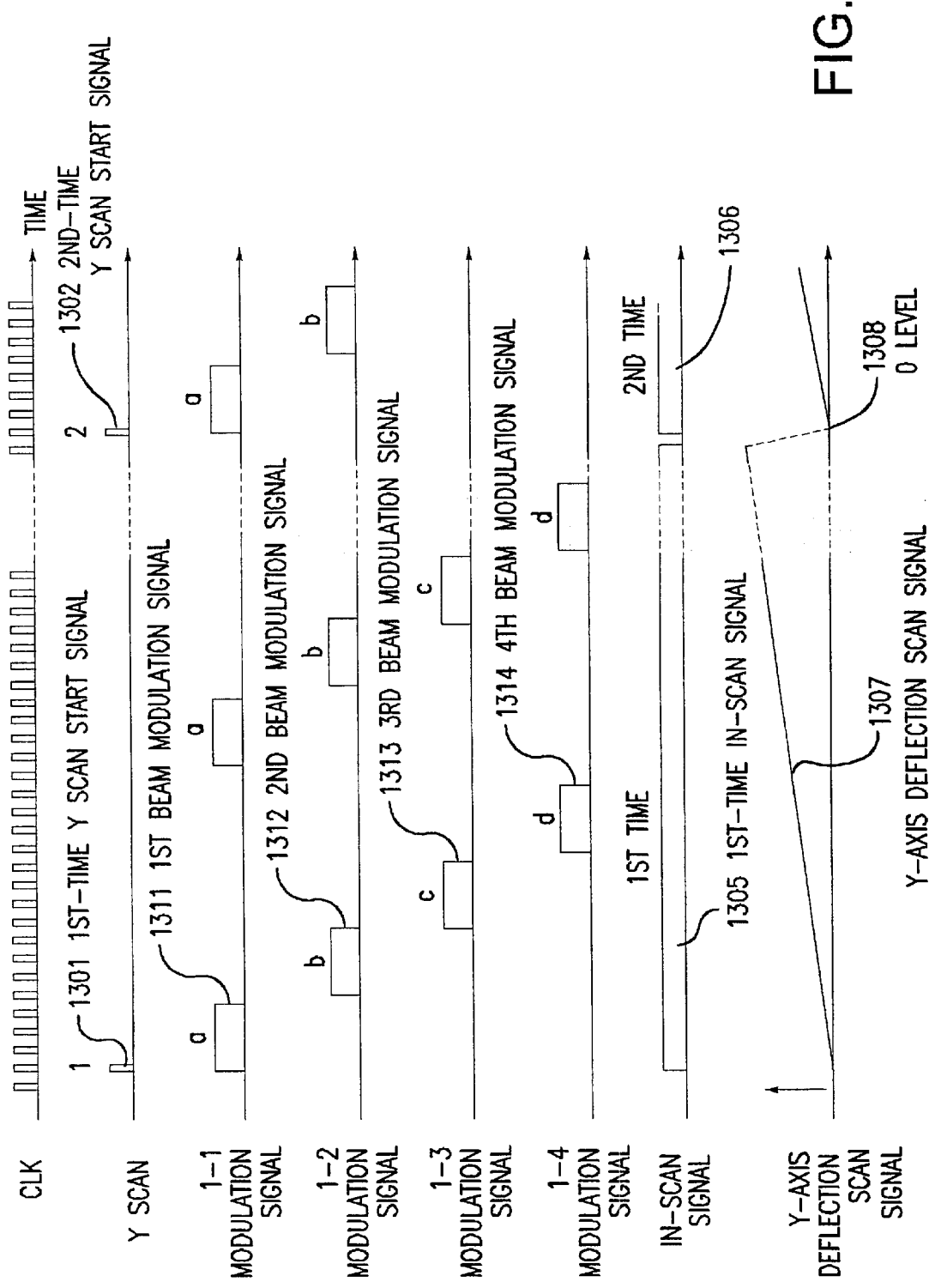
FIG. 13 is a timing chart of the deflection scan in the third embodiment of the present invention.

FIG. 13 is a timing chart of the deflection scan in the third embodiment of the present invention. In the figure, reference numeral 1301 denotes a first-time Y scan start signal, reference numeral 1302 a second-time Y scan start signal, reference numeral 1305 a first-time in-scan signal, reference numeral 1306 a second-time in-scan signal, reference numeral 1307 a Y-axis deflection scan signal, reference numeral 1308 the 0 level of the Y-axis deflection scan signal, reference numeral 1311 a first beam modulation signal, reference numeral 1312 a second beam modulation signal, reference numeral 1313 a third beam modulation signal, and reference numeral 1314 a fourth beam modulation signal.

Figure 14:
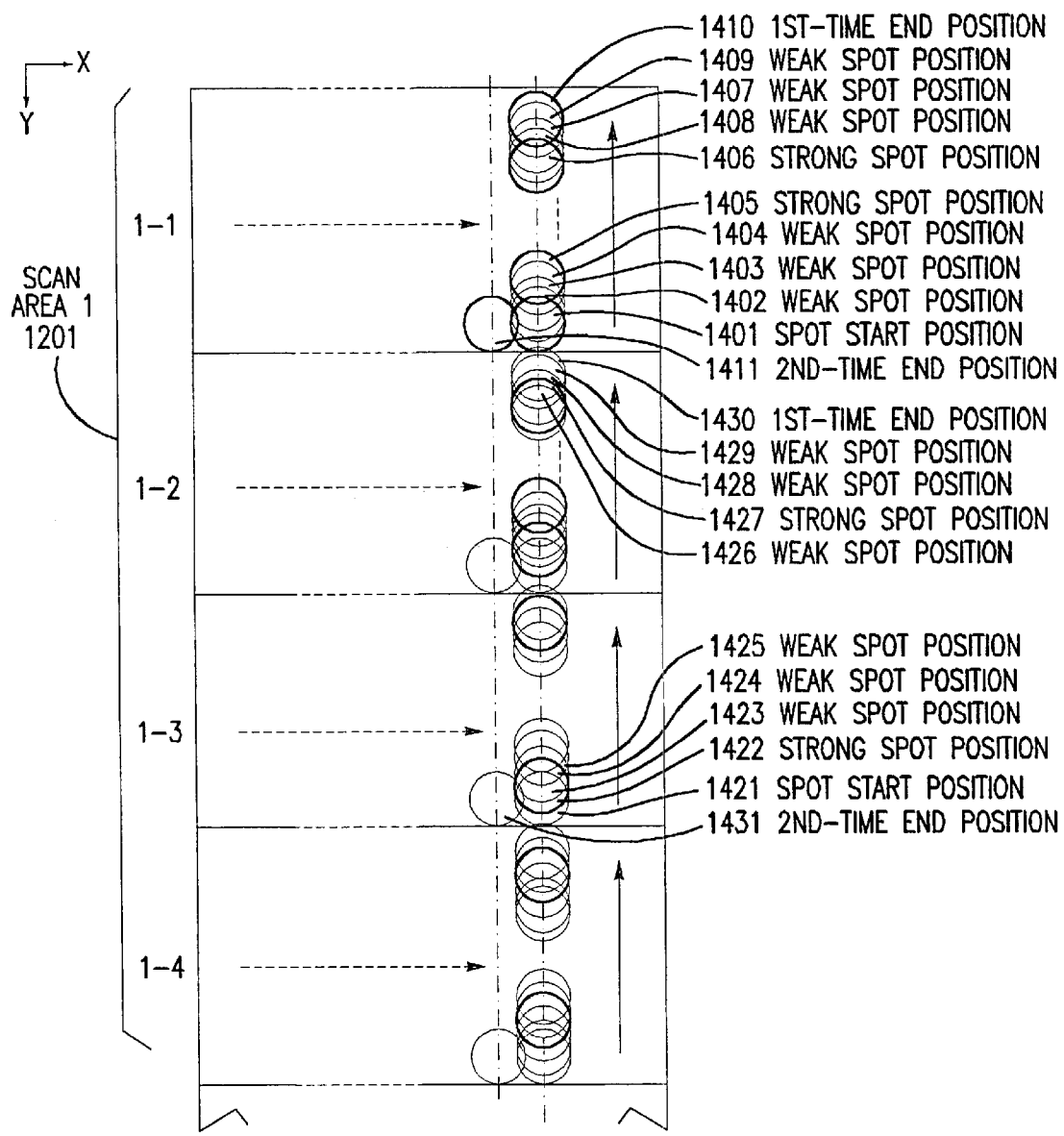
FIG. 14 is a schematic diagram illustrating a scan state of the laser beam in the third embodiment.

FIG. 14 is a schematic diagram illustrating a scan state of the laser beam in the third embodiment. In the figure, reference numeral 1210 denotes a scan area 1, reference numeral 1401 a first beam spot start position, reference numerals 1402, 1403, 1404, 1407, 1408, and 1409 weak spot positions, reference numerals 1405 and 1406 strong spot positions, reference numeral 1410 a first-time end position, reference numeral 1411 a second-time start position, reference numeral 1421 a second beam spot start position, reference numerals 1423, 1424, 1425, 1426, 1428, and 1429 weak spot positions, reference numerals 1422 and 1427 strong spot positions, reference numeral 1430 a first-time end position, and reference numeral 1431 a second-time start position.

Referring to FIG. 13, the laser beam to be radiated onto the scan area 1-1 is analog-modulated using the timing of a 1-1 modulation signal a, which is the first beam modulation signal 1311, the laser beam to be radiated onto the scan area 1-2 is analog-modulated using the timing of a 1-2 modulation signal b, which is the second beam modulation signal 1312, the laser beam to be radiated onto the scan area 1-3 is analog-modulated using the timing of a 1-3 modulation signal c, which is the third beam modulation signal 1313, and the laser beam to be radiated onto the scan area 1-4 is analog-modulated using the timing of a 1-4 modulation signal d, which is the fourth beam modulation signal 1314.

FIG. 14 shows a state in which the spots of the above-mentioned modulated laser beams operate on the test piece 1282. Details of branching the laser beam into four of FIG. 14 will be omitted from the following description because the two branched laser beams of FIG. 9 are simply converted to the four branched laser beams.

As shown in FIG. 14, in the scan area 1-1, the strong laser beam as indicated by thick-line circles 1401, 1404, 1406, 1410, 1411 and so on equivalent to the "ON" timing of the modulation signal a is radiated on the surface of the test piece 1282 and during "OPP" timing the weak laser beam of which intensity becomes nearly zero is radiated on the surface of the test piece 1282. In the scan area 1-2, the strong laser beam is radiated at the thick-line circles 1422, 1427 and so on equivalent to the timing of the modulation signal b and, when "OFF", the weak laser beam of which intensity becomes nearly zero is radiated.

Likewise, in the scan area 1-3, the strong laser beam is radiated in the timing of the modulation signal c. In the scan area 1-4, the strong laser beam is radiated in the timing of the modulation signal d. In another timing, the weak laser beam of which intensity becomes nearly zero is radiated.

Identification of the signals of the beams reflected from the test piece 1282 is made in the similar manner in which the identification is made in the second embodiment, except that the modulation timing for the branched laser beams is quartered instead of halved.

Briefly described, the reflected beams are detected by use of the modulation signals a, b, c, and d and the first-time in-scan signal 1305 in a time division manner as shown in FIG. 13. The reflected beam detect signal in the timing of the modulation signal a in the first-time in-scan signal 1305 of FIG. 13 is identified and detected as the reflected beam detect signal from the scan area 1-1 of FIG. 12, the reflected beam detect signal in the timing equivalent to the modulation signal b is identified by detected as the reflected beam detect signal from the scan area 1-2, the reflected beam detect signal in the timing of the modulation signal c is identified and detected as the reflected beam detect signal from the scan area 1-3, and the reflected beam detect signal in the timing of the modulation signal d is identified as the reflected beam detect signal from the scan area 1-4.

As for the scan area 2, the reflected beam detect signals are likely identified and detected by use of the second-time in-scan signal 1306 and the modulation signals a, b, c, and d. Although not shown, if there are scan areas 3, 4 and so on, the reflected beam detect signals are identified and detected in the same manner as above. Identification of the transmitted beam signals is made in the same manner, so that the description thereof will be omitted.

Figure 15:
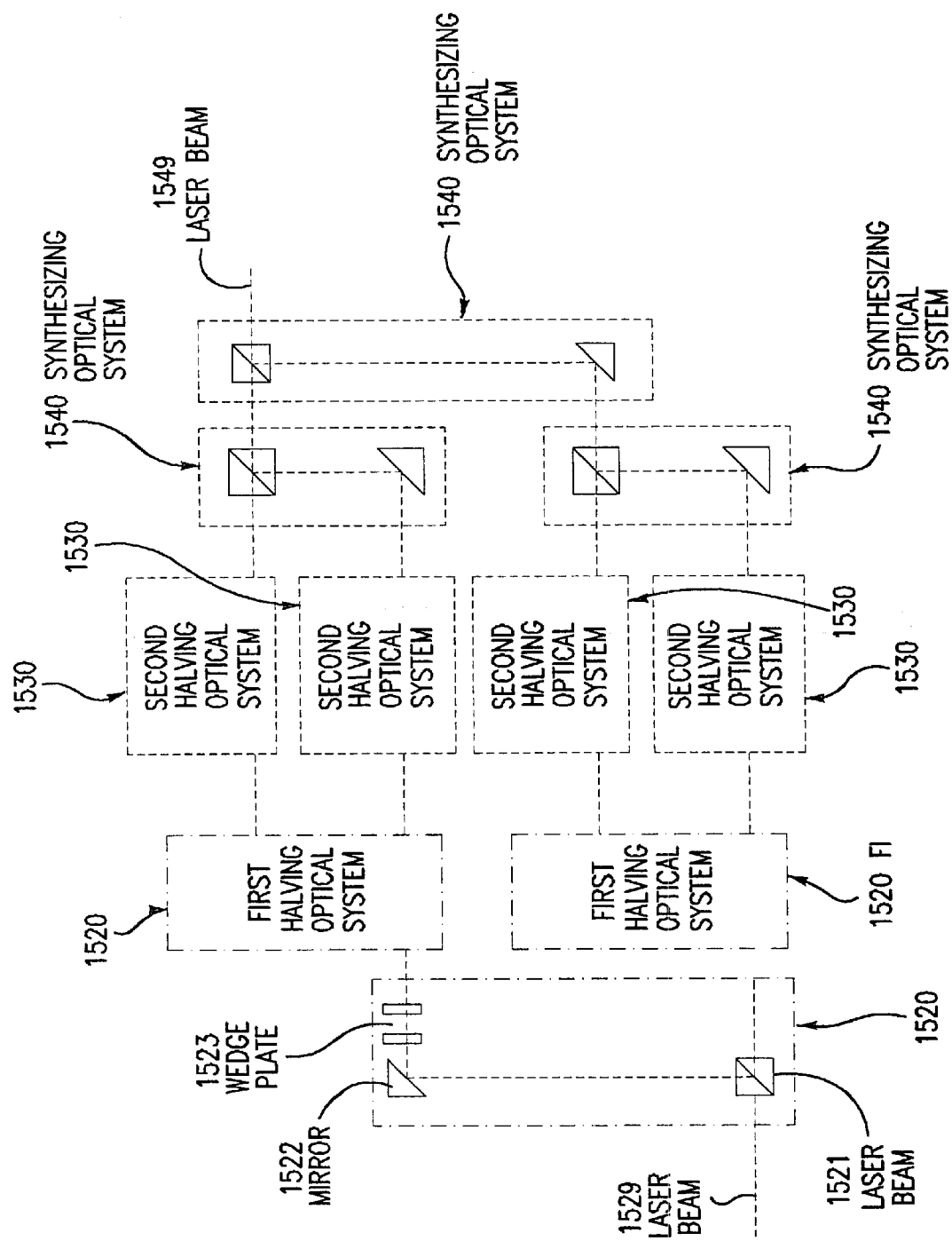
FIG. 15 is a general block diagram illustrating an optical system for splitting the laser beam into eight in the apparatus for inspecting high-precision patterns, practiced as a fourth embodiment of the invention.

FIG. 15 is a general block diagram illustrating an optical system for splitting the laser beam into eight in the apparatus for visually inspecting high-precision patterns, practiced as a fourth embodiment of the invention. In the figure, reference numeral 1520 denotes a first halving optical system, reference numeral 1521 a beam splitter, reference numeral 1522 a mirror, reference numeral 1523 a wedge plate, reference numeral 1529 a laser beam, reference numeral 1530 a second halving optical system, reference numeral 1540 a synthesizing optical system, and reference numeral 1549 a laser beam.

As shown in FIG. 15, it will be apparent that the laser beam 1529 may further be branched into eight, 10, 12, and so on.

It will also be apparent that the laser beam may be branched into odd numbers. For example, to branch the laser beam into five, the laser beam of the mirror 1522 of FIG. 15 may only be synthesized with another laser beam by skipping the next first halving optical system 1520 and the halving optical system 1530.

It will be further apparent that the technique of the second embodiment and the technique of the first embodiment using polarization may be used in combination. The present invention includes such a variation.

For the autofocusing method, the knife edge method using the split detector 177 in front of which the knife edge 179 is positioned is described. It will be apparent that, instead of the knife edge method, an astigmatic method using a collective lens having astigmatism and a quartering detector may be used.

What is claimed is:

1. A method of inspecting a surface of a test piece with a laser beam, comprising the steps of:

dividing the laser beam into a plurality of laser beams;

adding different features to respective divided laser beams for providing a different identification marker for each of said plurality of laser beams;

simultaneously scanning different portions of the surface of the test piece with responding independent laser beams having said different features;

forming an image of the surface of the test piece by using at least one of reflected and transmitted light for each of said plurality of marked laser beams, wherein said different identification marker comprises a different polarization state assigned to each of said plurality of marked laser beams.

2. A method of inspecting a surface of a test piece with a laser beam, comprising the steps of:

dividing the laser beam into a plurality of laser beams;

adding different features to respective divided laser beams for providing a different identification marker for each of said plurality of laser beams;

simultaneously scanning different portions of the surface of the test piece with responding independent laser beams having said different features;

forming an image of the surface of the test piece by using at least one of reflected and transmitted light for each of said plurality of marked laser beams, wherein said different identification marker comprises a variation in a light intensity assigned to each of said plurality of marked laser beams.

3. A method of inspecting a surface of a test piece with a laser beam, comprising the steps of:

dividing the laser beam into a plurality of laser beams;

adding different features to respective divided laser beams for providing a different identification marker for each of said plurality of laser beams;

simultaneously scanning different portions of the surface of the test piece with responding independent laser beams having said different features;

forming an image of the surface of the test piece by using at least one of reflected and transmitted light for each of said plurality of marked laser beams, wherein said laser beam has an ultraviolet wavelength.

4. An apparatus for inspecting a surface of a test piece with a laser beam, comprising:

a source of a laser beam;

a means for dividing said laser beam into a plurality of laser beams;

a means for adding different features to respective divided laser beams for assigning a plurality of identification markers;

a means for simultaneously scanning different portions of the surface of the test piece with responding independent laser beams having said different features, each of said plurality of marked laser beams simultaneously scanning a different portion of the surface of the test piece;

a means for detecting at least one of the light reflected from the surface of the test piece and the light transmitted through the surface of the test piece, wherein said detecting means detects light resulting from interaction of each of said plurality of marked laser beams with the surface of the test piece; and an image processing unit for identifying each of said plurality of marked laser beams by said plurality of identification markers and for detecting a defect in the surface of the test piece by obtaining an image of the surface of the test piece from said detecting means, wherein each of said plurality of identification markers comprises a different polarization state assigned to each of said plurality of marked laser beams.

5. An apparatus for inspecting a surface of a test piece with a laser beam, comprising:

a source of a laser beam;

a means for dividing said laser beam into a plurality of laser beams;

a means for adding different features to respective divided laser beams for assigning a plurality of identification markers;

a means for simultaneously scanning different portions of the surface of the test piece with responding independent laser beams having said different features, each of said plurality of marked laser beams simultaneously scanning a different portion of the surface of the test piece;

a means for detecting at least one of the light reflected from the surface of the test piece and the light transmitted through the surface of the test piece, wherein said detecting means detects light resulting from interaction of each of said plurality of marked laser beams with the surface of the test piece; and an image processing unit for identifying each of said plurality of marked laser beams by said plurality of identification markers and for detecting a defect in the surface of the test piece by obtaining an image of the surface of the test piece from said detecting means, wherein each of said plurality of identification markers comprises a variation in a light intensity assigned to each of said plurality of laser beams to form a plurality of marked laser beams.

6. The apparatus as claimed in claim 5, wherein said identification marker assigning means comprises an ultrasonic modulating means for analog modulation of each of said plurality of laser beams to change a light intensity thereof and a modulation signal generating means for outputting a modulation signal to said ultrasonic modulating means, said modulation signal controlling said light intensity of each of said plurality of marked laser beams in a time division manner.

7. An apparatus for inspecting a surface of a test piece with a laser beam, comprising:

a source of a laser beam;

a means for dividing said laser beam into a plurality of laser beams;

a means for adding different features to respective divided laser beams for assigning a plurality of identification markers;

a means for simultaneously scanning different portions of the surface of the test piece with responding independent laser beams having said different features, each of said plurality of marked laser beams simultaneously scanning a different portion of the surface of the test piece;

a means for detecting at least one of the light reflected from the surface of the test piece and the light transmitted through the surface of the test piece, wherein said detecting means detects light resulting from interaction of each of said plurality of marked laser beams with the surface of the test piece; and an image processing unit for identifying each of said plurality of marked laser beams by said plurality of identification markers and for detecting a defect in the surface of the test piece by obtaining an image of the surface of the test piece from said detecting means, wherein the laser beam has an ultraviolet wavelength.

* * * * *